United States Patent
Hlavka

(10) Patent No.: US 9,629,881 B2
(45) Date of Patent: *Apr. 25, 2017

(54) BACTERIOTHERAPY FOR CLOSTRIDIUM DIFFICILE COLITIS

(75) Inventor: Edwin J. Hlavka, Minneapolis, MN (US)

(73) Assignee: REBIOTIX, INC., Roseville, MN (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/576,573

(22) PCT Filed: Feb. 1, 2011

(86) PCT No.: PCT/US2011/000184
§ 371 (c)(1),
(2), (4) Date: Oct. 17, 2012

(87) PCT Pub. No.: WO2011/094027
PCT Pub. Date: Aug. 4, 2011

(65) Prior Publication Data
US 2013/0045274 A1    Feb. 21, 2013

Related U.S. Application Data

(60) Provisional application No. 61/337,283, filed on Feb. 1, 2010, provisional application No. 61/351,184, filed on Jun. 3, 2010.

(51) Int. Cl.
*A61K 35/74* (2015.01)
*C12N 1/04* (2006.01)
(Continued)

(52) U.S. Cl.
CPC ............... *A61K 35/74* (2013.01); *C12N 1/04* (2013.01); *C12N 1/20* (2013.01); *G01N 33/56911* (2013.01); *G01N 2333/33* (2013.01); *G01N 2800/52* (2013.01)

(58) Field of Classification Search
CPC .......... G06Q 50/22; G06Q 50/24; A61K 35/74
See application file for complete search history.

(56) References Cited

U.S. PATENT DOCUMENTS

| 3,317,675 A | 5/1967 | Harris et al. |
| 5,196,205 A | 3/1993 | Borody |

(Continued)

FOREIGN PATENT DOCUMENTS

| CA | 1330759 C | 7/1994 |
| CA | 1333564 C | 12/1994 |

(Continued)

OTHER PUBLICATIONS

Turnbaugh PJ, Ridaura VK, Faith JJ, Rey FE, Knight R, Gordon JI. The effect of diet on the human gut microbiome: a metagenomic analysis in humanized gnotobiotic mice. Sci Transl Med. Nov. 11, 2009;1(6).*

(Continued)

*Primary Examiner* — Jonathan K Ng
(74) *Attorney, Agent, or Firm* — Seager, Tufte & Wickhem, LLP

(57) ABSTRACT

This document discusses, among other things, receiving a plurality of donor fecal samples from a plurality of donors and storing and indexing each respective donor fecal samples using at least one characteristic of the respective donor fecal sample. In an example, the donor fecal sample can be screened and processed for subsequent use in fecal bacteriotherapy to displace pathogenic or undesired organisms in the digestive track of a patient with healthy or desirable gut micriobiota.

7 Claims, 3 Drawing Sheets

(51) Int. Cl.
*C12N 1/20* (2006.01)
*G01N 33/569* (2006.01) \

(56) References Cited

U.S. PATENT DOCUMENTS

| | | | |
|---|---|---|---|
| 5,229,374 | A | 7/1993 | Burton et al. |
| 5,274,001 | A | 12/1993 | Borody |
| 5,443,826 | A * | 8/1995 | Borody ............... 424/93.3 |
| 5,476,669 | A | 12/1995 | Borody |
| 5,519,014 | A | 5/1996 | Borody |
| 5,599,795 | A | 2/1997 | McCann et al. |
| 5,711,446 | A * | 1/1998 | Jeffs et al. ............. 220/23.83 |
| 5,858,403 | A | 1/1999 | Borody et al. |
| 5,925,354 | A | 7/1999 | Fuller et al. |
| 6,096,310 | A | 8/2000 | Bier |
| 6,103,268 | A | 8/2000 | Borody et al. |
| 6,132,767 | A | 10/2000 | Borody et al. |
| 6,214,341 | B1 | 4/2001 | Thomas, Jr. et al. |
| 6,426,338 | B1 | 7/2002 | Borody |
| 6,428,783 | B1 | 8/2002 | Khachatrian et al. |
| 6,635,260 | B1 | 10/2003 | Gerding |
| 6,645,530 | B1 | 11/2003 | Borody |
| 6,680,168 | B2 | 1/2004 | Thomas, Jr. et al. |
| 6,805,852 | B2 | 10/2004 | Lin et al. |
| 6,861,053 | B1 | 3/2005 | Lin et al. |
| 6,969,520 | B2 | 11/2005 | Thomas, Jr. et al. |
| 7,048,906 | B2 | 5/2006 | Lin et al. |
| 7,125,708 | B2 | 10/2006 | Wynne et al. |
| 7,307,062 | B2 | 12/2007 | Bolte |
| 7,607,776 | B1 | 10/2009 | Lewis et al. |
| 7,993,682 | B2 | 8/2011 | Borody et al. |
| 8,058,418 | B2 | 11/2011 | Boyle et al. |
| 8,110,177 | B2 | 2/2012 | Lin et al. |
| 8,460,648 | B2 | 6/2013 | Borody |
| 2002/0022019 | A1 | 2/2002 | Laulund |
| 2003/0031659 | A1 | 2/2003 | Farmer |
| 2003/0154105 | A1* | 8/2003 | Ferguson ............... 705/2 |
| 2003/0161871 | A1 | 8/2003 | Hird et al. |
| 2003/0180260 | A1 | 9/2003 | Clancy et al. |
| 2004/0028689 | A1 | 2/2004 | Borody |
| 2004/0062757 | A1 | 4/2004 | Finegold |
| 2004/0167062 | A1 | 8/2004 | Bolte |
| 2004/0170617 | A1 | 9/2004 | Finegold |
| 2004/0265291 | A1 | 12/2004 | Drake et al. |
| 2005/0074441 | A1* | 4/2005 | Collins et al. ............. 424/93.45 |
| 2005/0209883 | A1* | 9/2005 | Fletcher-Haynes et al. ..... 705/2 |
| 2005/0239706 | A1 | 10/2005 | Backhed et al. |
| 2005/0271749 | A1 | 12/2005 | Borody et al. |
| 2006/0008511 | A1 | 1/2006 | Lin et al. |
| 2006/0029608 | A1 | 2/2006 | Thomas et al. |
| 2006/0160121 | A1 | 7/2006 | Mounts et al. |
| 2006/0210448 | A1 | 9/2006 | Wang et al. |
| 2007/0178078 | A1 | 8/2007 | Khoo |
| 2007/0231336 | A1 | 10/2007 | Thomas, Jr. et al. |
| 2008/0027353 | A1 | 1/2008 | Kliman |
| 2008/0254009 | A1 | 10/2008 | Finegold |
| 2008/0269258 | A1 | 10/2008 | Breaker et al. |
| 2009/0148540 | A1 | 6/2009 | Martin et al. |
| 2009/0305253 | A1 | 12/2009 | Breaker et al. |
| 2010/0008850 | A1 | 1/2010 | Martin |
| 2010/0172874 | A1 | 7/2010 | Turnbaugh et al. |
| 2010/0316617 | A1 | 12/2010 | Renaud et al. |
| 2011/0123501 | A1 | 5/2011 | Chou et al. |
| 2011/0129529 | A1 | 6/2011 | Lin |
| 2011/0177976 | A1 | 7/2011 | Gordon et al. |
| 2011/0200570 | A1 | 8/2011 | Mosbaugh et al. |
| 2011/0223252 | A1 | 9/2011 | Borody et al. |
| 2012/0252775 | A1 | 10/2012 | Finegold |
| 2012/0276059 | A1 | 11/2012 | Boone et al. |
| 2012/0276060 | A1 | 11/2012 | Boone et al. |
| 2013/0022575 | A1 | 1/2013 | Cassity |
| 2013/0045274 | A1 | 2/2013 | Hlavka |
| 2013/0052172 | A1 | 2/2013 | Baker |
| 2013/0064885 | A1 | 3/2013 | Lin et al. |
| 2013/0108598 | A1 | 5/2013 | Oresic et al. |
| 2013/0149339 | A1 | 6/2013 | Honda et al. |
| 2013/0195804 | A1 | 8/2013 | Borody |
| 2013/0195820 | A1 | 8/2013 | Wacklin et al. |
| 2013/0266539 | A1 | 10/2013 | Borody |

FOREIGN PATENT DOCUMENTS

| | | | |
|---|---|---|---|
| CA | 1337265 | C | 10/1995 |
| CA | 2189418 | A1 | 5/1997 |
| CA | 2289717 | A1 | 11/1998 |
| CA | 2232001 | C | 12/2002 |
| CA | 2090220 | C | 7/2003 |
| CA | 2478135 | A1 | 9/2003 |
| CA | 2582137 | A1 | 2/2007 |
| CA | 2289717 | C | 2/2009 |
| CA | 2189418 | C | 7/2011 |
| CN | 1444484 | A | 9/2003 |
| CN | 102159084 | A | 8/2011 |
| DE | 3889547 | T2 | 11/1994 |
| DE | 68928665 | T2 | 11/1998 |
| EP | 0433299 | A1 | 6/1991 |
| EP | 0397689 | B1 | 5/1994 |
| EP | 0771562 | A2 | 5/1997 |
| EP | 1300472 | A1 | 4/2003 |
| EP | 0554291 | B1 | 12/2003 |
| EP | 0952773 | B1 | 11/2005 |
| EP | 0980246 | B1 | 12/2006 |
| EP | 2030623 | A1 | 3/2009 |
| EP | 1340078 | B1 | 5/2009 |
| EP | 1432786 | B1 | 7/2009 |
| EP | 0554291 | B2 | 10/2010 |
| EP | 2636684 | A1 | 9/2013 |
| JP | 2009-022280 | A | 2/2009 |
| WO | WO-89/03219 | A1 | 4/1989 |
| WO | WO-89/05659 | A1 | 6/1989 |
| WO | WO-90/01335 | A1 | 2/1990 |
| WO | WO-92/06690 | A1 | 4/1992 |
| WO | WO-96/11014 | A1 | 4/1996 |
| WO | WO-96/41615 | A2 | 12/1996 |
| WO | WO-97/09886 | A1 | 3/1997 |
| WO | WO-98/50043 | A1 | 11/1998 |
| WO | 0193904 | A1 | 12/2001 |
| WO | WO-01/97821 | A1 | 12/2001 |
| WO | WO-02/07741 | A1 | 1/2002 |
| WO | WO-03/002713 | A2 | 1/2003 |
| WO | WO-03/074061 | A1 | 9/2003 |
| WO | WO-2007/018563 | A2 | 2/2007 |
| WO | WO-2008/076696 | A2 | 6/2008 |
| WO | WO-2009/120347 | A2 | 10/2009 |
| WO | WO-2010/002890 | A2 | 1/2010 |
| WO | WO-2010/019208 | A1 | 2/2010 |
| WO | WO-2011/033310 | A1 | 3/2011 |
| WO | WO-2011/036539 | A1 | 3/2011 |
| WO | WO-2011/047439 | A1 | 4/2011 |
| WO | WO-2011/050397 | A1 | 5/2011 |
| WO | 2011094027 | A1 | 8/2011 |
| WO | WO-2011094027 | A1 | 8/2011 |
| WO | 2012013861 | A2 | 2/2012 |
| WO | 2012024638 | A2 | 2/2012 |
| WO | WO-2012/016287 | A2 | 2/2012 |
| WO | 2012033814 | A3 | 3/2012 |
| WO | WO-2012/033814 | A2 | 3/2012 |
| WO | 2012122478 | A1 | 9/2012 |
| WO | 2012122522 | A1 | 9/2012 |
| WO | 2012142605 | A1 | 10/2012 |
| WO | 2012149351 | A1 | 11/2012 |
| WO | 2013053836 | A1 | 4/2013 |
| WO | 2013090825 | A1 | 6/2013 |
| WO | 2013163582 | A1 | 10/2013 |
| WO | 2013171515 | A1 | 11/2013 |

OTHER PUBLICATIONS

Smith, T. "Fecal transplants to cure Clostridium difficile infection— Aetiology". http://scienceblogs.com/aetiology/2007/12/17/fecal-transplants-to-cure-clos/. Published on Dec. 17, 2007.*

Ley et al. "Worlds within worlds: evolution of the vertebrate gut microbiota". Nat Rev Microbiol. Oct. 2008 ; 6(10): 776-788.*

(56) References Cited

OTHER PUBLICATIONS

Roesch et al. "Influence of Fecal Sample Storage on Bacterial Community Diversity". Open Microbiol J. 2009; 3: 40-46.*
Achá et al., "Changes of viability and composition of the *Escherichia coli* flora in faecal samples during long time storage," Journal of Microbiological Methods (Dec. 1, 2005) 63: 229-238. XP027746380.
Bakken, J.S., "Fecal bacteriotherapy for recurrent *Clostridium difficile* infection," Anaerobe (Jan. 1, 2009) 15: 285-289. XP009161367.
Hopkings et al., "Variation in human intestinal microbiota with age," Digest and Liver Disease (Sep. 1, 2002) 34 (Suppl. 2): S12-S18. XP055095077.
Ott et al., "In vitro alterations of intestinal bacterial microbiota in fecal samples during storage," Diagnostic Microbiology and Infectious Disease (Dec. 1, 2004) 50: 327-245. XP004669529.
Supplemental European Search Report for corresponding EP Application No. 11737418.1 mailed on Jan. 16, 2014.
Frantzen, M. et al, Microbe preservation, Emperical evaluation of preservation methods for faecal DNA, 1998.
Freeman, J.; Wilcox, M.H., Microbe preservation, The effects of storage conditions on viability of Clostridium difficile vegetative cells and spores and toxin activity in human faeces, 2003.
Kelson, J.; Wu, G., Microbiome papers, The gut microbiota, environment and diseases of modern society, 2012.
Moschen, A. et al, Microbiome papers, Dietary Factors: Major Regulators of the Gut's Microbiota, 2012.
Gravitz, L, Microbiome papers, The critters within, 2012.
Green, H. et al, Microbe preservation, Impact of Freezing on the Future Utility of Archived Surveillance Culture Specimens, 2007.
Grzeskowiak, L. et al, Pediatrics, Distinct Gut Microbiota in Southeastern African and Northern European Infants, 2011.
Gueimonde, M. et al, Analysis of Species in Feces, New real-time quantitative PCR procedure for quantification of bifidobacteria in human fecal samples, 2004.
Nature Publishing Group, Industry, Recent patent applications in bacteriotherapy, 2013.
Brown, J. et al, Microbiome papers, Translating the human microbiome, 2013.
Giniatullina, A. et al, Industry, Building for Big Pharma, 2013.
Hansen, R. et al, Pediatrics, Microbiota of De-Novo Pediatric IBD: Increased Faecalibacterium Prausnitzii and Reduced Bacterial Diversity in Crohn ' s But Not in Ulcerative Colitis, 2012.
Hecht, GA et al, Industry, What's the Value of an FDA IND for Fecal Microbiota Transplantation in Clostridium difficile Infection?, 2013.
Hoefman, Microbe preservation, Survival or Revival: Long-Term Preservation Induces a Reversible Viable but Non-Culturable State in Methane-Oxidizing Bacteria, 2012.
Hoffman, Christian, Microbe papers, The human intestinal microbiome and dietary patterns, 2011.
Honda, H.; Dubberke, E., C Diff Studies, The changing epidemiology of Clostridium difficile infection, 2014.
Hsiao, E. et al, Microbiome papers, Microbiota Modulate Behavioral and Physiological Abnormalities Associated with Neurodevelopmental Disorders, 2013.
Iida, N. et al, Cancer, Supplimentary Materials for Commensal Bacteria Control Cancer Response to Therapy by Modulating the Tumor Microenvironment, 2013.
Jernberg, C. et al, Microbiome papers, Long-term ecological impacts of antibiotic administration on the human intestinal microbiota , 2007.
Calabrese, R. et al, Industry, Finding common ground with ISO 9001 and FDA Good Manufacturing Practices, 2013.
Jakobbsson, Hedvig et al, Microbiome papers, Short-Term Antibiotic Treatment Has Differing Long-Term Impacts on the Human Throat and Gut Microbiome, 2010.
Jansson, Janet, GI Disease—General, Microbiota and Inflammatory Bowel Disease (presentation), 2011.
Jeffery, I. et al, GI Disease—General, An irritable bowel syndrome subtype defined by species-specific alterations in faecal microbiota, 2013.
Jump, R. et al, C Diff Studies, Tigecycline Exhibits Inhibitory Activity against Colostridium difficile in the colon of Mice and does not promote growth or toxin production, 2013.
Kaaskoush, N. et al, Pediatrics, Chrohn's, Microbial Dysbiosis in Pediatric Patients with Crohn's Disease, 2012.
Russell, G. et al, FMT Studies and Reviews, Fecal bacteriotherapy for relapsing colostridium difficile infection in a child: a proposed treatment protocol, 2010.
Kahn, S. et al, Ulcerative Colitis, Fecal Bacteriotherapy for Ulcerative Colitis: Patients Are Ready, Are We?, 2012.
Karlsson, F. et al, Microbiome papers, Gut metagenome in European women with normal, impaired and diabetic glucose control, 2013.
Karmali, S. et al, Industry, CAGS Clinical Practice Committee report: the science of Clostridium difficile and surgery, 2013.
Keller, J.; Surawicz, C., C Diff Studies, Clostridium difficile Infection in the Elderly, 2014.
Kellermayer, Richard, Pediatrics, Prospects and challenges for intestinal microbiome therapy in pediatric gastrointestinal disorders, 2013.
Kelly, C. et al, Industry, A How to Guide: Investigational New Drug Application for Fecal Microbiota Transplantation, 2013.
Koboziev, I. et al, Microbiome papers, Role of the Enteric Microbiota in Intestinal Homeostasis and Inflammation, 2013.
Koeth, R. et al, Microbiome papers, Intestinal microbiota metabolism of I-carnitine, a nutrient in red meat, promotes atherosclerosis, 2013.
Konstantinov, S. Peppelenbosch, M., FMT Studies and Reviews, Fecal Microbiota Transfer May Increase Irritable Bowel Syndrome and Inflammatory Bowel Diseases—Associated Bacteria, 2013.
Kuk, S. et al, Microbial Preservation, Stool sample storage conditions for the preservation of Giardia intestinalis DNA, 2012.
Kumar, P. et al, Pediatrics, Comparative analysis of fecal microflora of healthy full-term Indian infants born with different methods of delivery (vaginal vs cesarean): Acinetobacter sp. prevalence in vaginally born infants, 2012.
Kunde, S. et al, Pediatrics, Safety, Tolerability, and Clinical Response After Fecal Transplantation in Children and Young Adults With Ulcerative Colitis, 2013.
Lagier, J. et al, Microbiome papers, Microbial culturomics: paradigm shift in the human gut microbiome study, 2012.
Laksminarayana, B. et al, Analysis of Species in Feces, Prevalence and characterization of Clostridium perfringens from the faecal microbiota of elderly Irish subjects, 2013.
Landy, J. et al, FMT Studies and Reviews, Review article: faecal transplantation therapy for gastrointestinal disease, 2011.
Lemon, Katherine, Microbiome papers, Microbiota-Targeted Therapies: An Ecological Perspective, 2012.
Lo Vecchio, A; Cohen, M., FMT Studies and Reviews, Fecal microbiota transplantation for Clostridium difficile infection: benefits and barriers, 2013.
Louie, T. et al, C Diff Studies, Fidaxomicin Preserves the Intestinal Microbiome During and After Treatment of Clostridium difficile Infection (CDI) and Reduces Both Toxin Reexpression and Recurrence of CDI, 2012.
Maukonen, J. et al, Analysis of Species in Feces, The currently used commercial DNA-extraction methods give different results of clostridial and actinobacterial populations derived from human fecal samples, 2011.
Patel, N. et al, FMT Studies and Reviews, Fecal Microbiota Transplant for Recurrent Colostridium difficile Infection: Mayo Clinic in Arizona Experience, 2013.
McDonald, C. et al, C Diff Studies, Colostridium difficile infection in patients discharged from U.S. short-stay hospitals, 1996-2003, 2006.
Momozawa, Y. et al, Analysis of Species in Feces, Characterization of Bacteria in Biopsies of Colon and Stools by High roughput Sequencing of the V2 Region of Bacterial 16S rRNA Gene in Human, 2011.

(56) References Cited

OTHER PUBLICATIONS

Mukhopadhyay, S.; Linstedt, A., Microbiome papers, Manganese Blocks Intracellular Trafficking of Shiga Toxin and Protects Against Shiga Toxicosis, 2012.
Munukka, E. et al, Microbiome papers, Women With and Without Metabolic Disorder Differ in Their Gut Microbiota Composition, 2012.
"International Application Serial No. PCT/US2011/000184 Search Report mailed Apr. 8, 2011", 21 Pgs.
"International Application Serial No. PCT/US2011/000184, Written Opinion mailed Apr. 8, 2011", 21 pgs.
Aas, et al., "Recurrent Clostridium difficile Colitis:", Case Series Involving 18 Patients Treated with Donor Stool Administered via a Nasogastric Tube, Clin Infect Dis, vol. 36, (Mar. 1, 2003), entire document, especially: p. 581, col. 2, para 4-p. 582, col. 2, para 3; p. 583, Table 2, Table 4, pp. 580-585.
Gough, E., et al., "Systematic Review of Intestinal Microbiota Transplantation (Fecal Bacteriotheraphy) for Recurrent Clostridium difficile Infection", (2011), 994-1002.
Office Action for corresponding Canadian Application No. 2788558 mailed on Jun. 13, 2013.
"International Application Serial No. PCT/US2011/000184, International Preliminary Report on Patentability mailed Aug. 16, 2012", 9 pgs.
Murri, M. et al, Pediatrics, Gut microbiota in children with type 1 diabetes differs from that in healthy children: a case-control study, 2013.
HMPC (Multiple Authors), Microbiome papers, Structure, function and diversity of the healthy human microbiome, 2012.
Mole, Beth, Industry, FDA gets to grips with Faeces, 2013.
Lozupone, C. et al, Microbiome papers, Diversity, stability and resilience of the human gut microbiota, 2012.
Wesemann, D. et al, Pediatrics, Microbial colonization influences early B-lineage development in the gut lamina propria, 2013.
David, L. et al, Microbiome papers, Diet rapidly and reproducibly alters the human gut microbiome, 2013.
Lowy, I. et al, C Diff Studies, Treatment with Monoclonal Antibodies against Colostridium difficile Toxins, 2010.
Nieuwdorp, Max, Microbiome papers, Gut microbiota determine insulin sensitivity, 2013.
Wu, G. et al, Microbiome papers, Linking long-term dietary patterns with gut microbial enterotypes, 2011.
Schloissnig, S. et al, Microbiome papers, Genomic variation landscape of the human gut microbiome, 2013.
Young, Vincent, Microbiome papers, The Intestinal Microbiota in Health and Disease, 2012.
Dethlefsen, L; Reiman, D., Microbiome papers, Incomplete recovery and individualized responses of the human distal gut microbiota to repeated antibiotic perturbation, 2010.
Henning, Torsten, Industry, Polyethylene glycols (PEGs) and the pharmaceutical industry, 2002.
Khanna, S.; Tosh, P., Industry, A Clinician's Primer on the Role of the Microbiome in Human Health and Disease, 2014.
Multiple pharma companies, Industry, Rare Diseases: A report on orphan drugs in the pipline, 2013.
Nitzan, O. et al, Industry, Clostridium difficile and inflammatory bowel disease: Role in pathogenesis and implications in treatment, 2013.
Noverr, M.; Huffnagle, G., Microbiome papers, Does the microbiota regulate immune responses outside the gut?, 2004.
Nyangale, E. et al, Microbiome papers, Gut Microbial Activity, Implications for Health and Disease: The Potential Role of Metabolite Analysis, 2012.
Ohtake, S. et al, Microbiome papers, Formulation and Stabilization of Francisella tularensis Live Vaccine Strain, 2011.
Onouchi, S. et al, Cancer, PCR-based Assessment of the Recovery Rate of Exfoliated Colonocytes or Cancer Cells from Fecal Samples Depends on the Storage Conditions after Defecation, 2007.
O'Sullivan, O. et al, Microbiome papers, Alterations in intestinal microbiota of elderly Irish subjects post-antibiotic therapy, 2013.
O'Toole, P.W., Microbiome papers, Changes in the intestinal microbiota from adulthood through old age, 2012.
Ott, Stephan et al, Microbial Preservation, in vitro alterations of intestinal bacterial micribiota in fecal samples though storage, 2004.
Papa, E. et al, Pediatrics, Non-Invasive Mapping of the Gastrointestinal Microbiota Identifies Children with Inflammatory Bowel Disease, 2012.
Pisano, R. et al, Industry, Quality by design: scale-up of freeze-drying cycles in the pharmaceutical industry, 2013.
Schloissnig, S. et al, Microbiome papers, Geniomic variation landscape of the human gut microbiome, 2013.
Pamer, E.G., FMT Studies and Reviews, Fecal microbiota transplantation: effectiveness, complexities, and lingering concerns, 2014.
Prideaux, L. et al, GI Disease—General, Inflammatory bowel disease in Asia: A systemic review, 2012.
Qin, J. et al, Microbiome papers, A metagenome-wide association study of gut miocrobiota in type 2 diabetes, 2012.
Roesch, L. et al, Microbial Preservation, Influence of fecal sample storage on bacterial community diversity, 2009.
Rubin, D. et al, GI Disease—General, Chronic intestinal inflammation: inflammatory bowel disease and colitis-associated colon cancer, 2012.
Savini, M. et al, Cryopreservation Studies, Pilot-scale Production and Viability Analysis of Freeze-Dried Probiotic Bacteria Using Different Protective Agents, 2010.
Gophna, Uri, Microbiome papers, The guts of dietary habits, 2011.
Pennisi, E., Cancer, Cancer therapies use a little help from microbial friends, 2013.
Viaud, S. et al, Microbiome papers, The intestinal microbiota modulates the anticancer immuni effects of cyclophosphamide, 2013.
Viaud, S. et al, Microbiome papers, Supplementary materials for: The intestinal microbiota modulates the anticancer immuni effects of cyclophosphamide, 2013.
Segata, N. et al, Microbiome papers, Composition of the adult digestive tract bacterial microbiome based on seven mouth surfaces, tonsils, throat and stool samples, 2012.
Shamekhi, F. et al, Drug Delivery, Cell viability of microencapsulated Bifidobacterium animalis subsp. lactis under freeze-drying, storage and gastrointestinal tract simulation conditions, 2013.
Simoes, C. et al, Analysis of Species in Feces, Habitual Dietary Intake is Associated with Stool Microbiota Composition in Monozygotic Twins, 2013.
Sobhani, I. et al, GI Disease—General, Microbial dysbiosis and colon carcinogenesis: could colon cancer be considered a bacteria-related disease?, 2013.
Song, Y. et al, FMT Studies and Reviews, Microbiota dynamics in patients treated with fecal microbiota transplantation for recurrent clostridium difficile infection, 2013.
Stern, A. et al, Microbiome papers, CRISPR targeting reveals a reservoir of common phages associated with the human gut microbiome, 2012.
Clarke, S. et al, Microbiome papers, The gut microbiota and it's relationship to diet and obesity, 2012.
Surawicz, C. et al, Industry, Guidelines for diagnosis, treatment and prevention of clostridium difficile infections, 2013.
Tannock, Gerald, Microbiome papers, The bowel microbiota and inflammatory bowel diseases, 2010.
Tjellstrom, B. et al, Pediatrics, Effect of exclusive enteral nutrition on gut microflora function in children with Chron's disease, 2012.
Tottey, W. et al, Microbiome papers, The Human Gut Chip "HuGChip", an Explorative Phylogenetic Microarray for Determining Gut Microbiome Diversity at Family Level, 2013.
Van Nood, E. et al, FMT Studies and Reviews, Fecal microbiota transplantation: facts and controversies, 2014.
Varela, E. et al, Ulcerative Colitis, Colonisation by Faecalibacterium prausnitzii and maintenance of clinical remission in patients with ulcerative colitis, 2013.
Vigsnaes, L. et al, Ulcerative Colitis, Microbiotas from UC patients display altered metabolism and reduced ability of LAB to colonize mucus, 2012.
Agar Plate Info, BBL Bacteroides Bile Esculin Agar (BBE), 2006.

(56) References Cited

OTHER PUBLICATIONS

Plate Info, BBL CDC Anaerobe 5% Sheep Blood Agar, 2006.
Reynolds, Jackie, Agar Plate Info, Serial Dilution Protocol ASM, 2012.
Franks, Alison et al, Analysis of Species in Feces, Variations of Bacterial Populations in Human Feces Measured by Fluorecent in Situ Hybridization with Group-Specific 16S rRNA-Targeted Oligonucleotide Probes, 1998.
Goodman, Andrew et al, Analysis of Species in Feces, Extensive Personal Human Gut Microbiota Culture Collections Characterized and Manipulated in Gnotobiotic Mice, 2011.
Hill, M.J. et al, Analysis of Species in Feces, The normal chronic bacterial flora, 1975.
Harmsen, HJM et al, Analysis of Species in Feces, Comparison of viable cell counts and fluorscent in situ hybridization using specific rRNA-based probes for the quantification of human fecal bacteria, 1999.
Cotta, Michael et al, Analysis of Species in Feces, Isolation, characterization and comparison of bacteria from swine faeces and manure storage pits, 2003.
Chang, Ju Young et al, Analysis of Species in Feces, Decreased diversity of the fecal microbiome in recurrent clostridium difficile-associated diarrhea, 2008.
Ben-Amor, Kaouther et al, Analysis of Species in Feces, Genetic diversity of viable, injured and dead fecal bacteria assessed by fluorecence-activated cell sorting and 16S rRNA gene analysis, 2005.
Khortus, Alexander et al, Analysis of Species in Feces, Changes in the composition of the human fecal microbiome after bacteriotherapy for recurrent clostridium difficile associated diahrrea, 2010.
MacNeal, Ward et al, Analysis of Species in Feces, The fecal bacteria of health men, 1909.
Moore, WEC et al, Analysis of Species in Feces, Human fecal flora: the normal flora for 20 Japanese-Hawaiians, 1974.
Rinttila, T et al, Analysis of Species in Feces, Development of an extensive set of 16S rDNA-targeted primers for quantifiation of pathogenic and indigenous bacteria in faecal samples by real-time PCR, 2004.
Stephen, Alison et al, Analysis of Species in Feces, The microbial contribution to human fecal mass, 1980.
Zoetendal, erwin et al, Analysis of Species in Feces, Mucosa-Associated bacteria in the human gastrointestinal tract are uniformly distributed along the colon and differ from the community recovered from feces, 2002.
Haines, R B, Bacterial Presentation via Freezing, The effect of freezing on bacteria, 1938.
Zhao, G et al, Bacterial Presentation via Freezing, Effect of protective agents, freezing temperature, rehydration media on viability of malolactic bacteria subjected to freeze-drying, 2005.
Hamilton, Matthew et al, Bacterial Presentation via Freezing, Standardized frozen preparation for transplantation of fecal microbiota for recurrent clostridium difficile infection, 2012.
Teather, Ronald, Bacterial Presentation via Freezing, Maintenance of Laboratory Strains of Obligaetly Anaerobic Rumen Bacteria, 1982.
Swift, Homer, Bacterial Presentation via Freezing, Preservation of stock cultures of bacteria by freezing and drying, 1921.
Proom, H. et al, Bacterial via Freezing, The drying and preservation of bacterial cultures, 1948.
Dubberke, ER et al, C Diff Studies, The ecology and pathobiology of clostridium difficile infections: an interdisciplinary challenge, 2001.
Kyne, Lorraine et al, C Diff Studies, Asymptomatic carriage of clostridium difficile and serum levels of IgG antibody angainst toxin A, 2000.
MacFarland, Lynne et al, C Diff Studies, Recurrent clostridium difficile disease: epidemiology and clinical characteristics, 1999.
Holy, Ondrej et al, C Diff Studies, Oxygen tolerance in anaerobic pathogenic bacteria, 2012.
Bakken, Johan et al, C Diff Treatment with Fecal Transplant, Treating clostridium difficile infection with fecal microbiota transplantation, 2011.
Silverman, Michael et al, C Diff Treatment with Fecal Transplant, Success of self-administered home fecal transplantation for chronic clostridium difficile infection, 2010.
Sokol, H et al, Analysis of Species in Feces, Low counts of Faecalibacterium prausnitzii in colitis microbiota, 2009.
Olson, Mary et al, C Diff Treatment with Fecal Transplant, 10 years of prospective clostridium difficile associated disease surveillance and treatment at the Minneapolis VA medical center, 1994.
Floch, Martin, C Diff Treatment with Fecal Transplant, Fecal bacteriotherapy, fecal transplant and the microbiome, 2010.
Khortus, Alexander et al, C Diff Treatment with Fecal Transplant, Therapeutic transplantation of the distal gut microbiome, 2010.
vanNood, E et al, C Diff Treatment with Fecal Transplant, Struggling with recurrent clostridium difficile infections: is donor faeces the solution?, 2009.
Amann, RI et al, Counting Bacteria, Combination of 16S rRNA-targeted oligonucleotide probes with flow cytometry for analyzing mixed microbial populations, 1990.
Maturin, Larry et al, Counting Bacteria, Bacteriological analytical manual chap 3: aerobic plate count, 2001.
Alsharif, R., et al., Counting Bacteria, Bacterial detection and live/dead discrimination by flow cytometry, 2002.
Counting Bacteria, Live/Dead BacLight bacterial viability kits, 2008.
Ben-Amor, Kaouther et al, Counting Bacteria, Multiparametric flow cytometry and cell sorting for the assessment of viable, injured, and dead bifidobacterium cells during bile salt stress, 2002.
Gasol, Joseph et al, Counting Bacteria, Using flow cytometry for counting natural planktonic bacteria and understanding the structure of planktonic bacterial communities, 2000.
Dan, M et al, Fecal Preservation, Comparison of preservation media and freezing conditions for storage of specimens of faeces, 1989.
Gut Microbiome News, Articles highlight advances, potential applications of gut microbiome research, 2012.
Backhed, Fredrik et al, Gut Microbiome News, Host-Bacterial mutualism in the human intestine, 2005.
Gut Microbiome News, Consortium members publish collection of studies stemming from human microbiome project, 2005.
O'Hara, Ann et al, Gut Microbiome News, The gut flora as a forgotten organ, 2006.
Saulnier, Delphine et al, Gut Microbiome News, Gastrointestinal microbiome signatures of pediatric patients with irritable bowel syndrome, 2001.
Gut Microbiome News, Structure, function and diversity of the healthy human microbiome, 2012.
Rechner, Paula et al, C Diff Studies, Clinical Features of Clostridil Bacteremia: A review from a rural area, 2001.
Postgate, JR et al, Bacterial Presentation via Freezing, On the survival of frozen bacteria, 1961.
Liao, CH et al, Bacterial Survival in different soln, Survivability and long-term preservation of bacteria in water and in phosphate-buffered saline, 2002.
Kozak et al., "Antimicrobial resistance in *Escherichia coli* isolates from swine and wild small mammals in the proximity of swine farms and in natural environments in Ontario, Canada," Applied and Environmental Microbiology (Feb. 2009) 75 (3): 559-566.
Pray, L.; Pillsbury, L.; Tomayko, E., Microbiome papers, The human microbiome, diet and health, 2013.
Lin, HJ. et al, C Diff Studies, Risk factors for colostridium difficile associated diarrhea among hospitalized adults with fecal toxigenic C. difficile colonization, 2013.
Wu, T. et al, Analysis of Species in Feces, Gut microbiota dysbiosis and bacterial community assembly associated with cholesterol gallstones in large-scale study, 2013.
Liu, Z.; Cao, A.; Gong, Y.,Microbiome papers, Microbiota regulation of inflammatory bowel disease and colorectal cancer, 2013.
Gareau, M; Barrett, K., Gut Microbiome News, Fluid and electrolyte secretion in the inflamed gut: Novel targets for treatment of inflammation induced diarrhea, 2013.

(56) References Cited

OTHER PUBLICATIONS

Rubin, David, Ulcerative Colitis, Curbing our enthusiasm for fecal transplantation in ulcerative colitis, 2013.
Angelberger, S. et al, Ulcerative Colitis, Temporal bacterial community dynamics vary among uncerative colitis patients after fecal microbiota transplantation, 2013.
Friedman, ND et al, C Diff Studies, Prevalence of colostridium difficile colonization among healthcare workers, 2013.
Orenstein, R.; Griesbach, C.; DiBaise, J., General FMT News and Regulations, Moving fecal microbiota transplantation into the mainstream, 2013.
BD, Agar Plate Info, Brucella Blood Agar with Hemin and Vitamin K1, 2011.
Merlino, J. et al, Agar Plate Info, Evaluation of CHROMagar Orientation for differentiation and presumptive identification of Gram negative bacilli and Enterococcus species., 1996.
Azad, M. et al., Pediatrics, Gut microbiota of healthy canadian infants: profiles by mode of delivery and infant diet at 4 months, 2013.
Arthur, J.; Jobin, C., Cancer, The struggle within: microbial influences on colorectal cancer, 2011.
Andoh, A. et al, Chrohn's Disease, Multicenter analysis of fecal microbiota profiles in Japanese patients with Chron's disease, 2012.
Acha, S.J. et al, Microbe preservation, Changes of viability and composition of the *Escherichia coli* flora in faecal samples during long term storage, 2005.
Abujamel, T. et al, C Diff Studies, Defining the vulnerable period for re-establishment of Colostridium difficile colonization after treatment of C. difficile infection with oral vancomycin or metronidazole, 2013.
Bahl, et al, Microbe preservation, Freezing fecal samples prior to DNA extraction affects the Firmicutes to Bacteroidetes ratio determined by downstream quantitative PCR analysis, 2011.
Barr, David, Industry, CGMPs in the production of clinical supplies, 2007.
Bauer, et al, C Diff Studies, Patients with cystic fibrosis have a high carriage rate of non-toxigenic Clostridium difficile, 2013.
Benjamin, et al, Chrohn's Disease, Smokers with Active Crohn's Disease Have a Clinically Relevant Dysbiosis of the Gastrointestinal Microbiota, 2011.
Bervoets, L. et al, Pediatrics/Obesity Related, Differences in gut microbiota composition between obese and lean children: a cross-sectional study, 2013.
Best, E. et al, Industry, The Potential for Airborne Dispersal of Clostridium difficile from Symptomatic Patients, 2012.
Bhat, A. et al, Cryopreservation Studies, Bacillus subtilis natto: a non-toxic sourse of poly-γ-glutamic acid that could be used as a cryoprotectanc for probiotic bactera, 2013.
Bodger, K. et al, Industry, Development and validation of a rapid,generic measure of disease control from the patient's perspective: the IBD-Control questionnaire, 2013.
Borody, TJ et al, FMT Studies and Reviews, Therapeutic faecal microbiota transplantation: current status and future developments, 2014.
Cardona, S. et al, Microbe preservation, Storage conditions of intestinal microbiota matter in metagenomic analysis, 2012.
Pathak, et al, FMT Studies and Reviews, Treatment of relapsing Clostridium difficile infection using fecal microbiota transplantation, 2013.
CDC, Industry, Antibiotic resistance threats in the United States, 2013, 2013.
Chandel, N; Budlinger, G.R., Industry, The good and bad of antibiotics, 2013.
Chassard, C. et al, GI Disease—General, Functional dysbiosis within the gut microbiota of patients with constipated-irritable bowel syndrome, 2011.
Claas, E. et al, Analysis of Species in Feces, Performance of the xTAGR Gastrointestinal Pathogen Panel, a Multiplex Molecular Assay for Simultaneous Detection of Bacterial, Viral, and Parasitic Causes of Infectious Gastroenteritis, 2013.
Clemente, J. et al, Microbiome papers, The Impact of the Gut Microbiota on Human Health: An Integrative View, 2012.
Cnops, L.; Van Esbroeck, M., Bacterial Preservation via Freezing, Freezing of stool samples improves real-time PCR detection of Entamoeba dispar and Entamoeba histolytica, 2010.
Comito, D.; Romano, C., Pediatrics, Dysbiosis in the Pathogenesis of Pediatric Inflammatory Bowel Diseases, 2012.
Cox, L.; Blaser, M., Obesity Related, Pathways in Microbe-Induced Obesity, 2013.
Damman, C. et al, FMT Studies and Reviews, The Microbiome and Inflammatory Bowel Disease: Is There a Therapeutic Role for Fecal Microbiota Transplantation?, 2012.
De Cruz, P. et al, Analysis of Species in Feces, Characterization of the Gastrointestinal Microbiota in Health and Inflammatory Bowel Disease, 2012.
De Goffau, M. et al, Pediatrics, Fecal Microbiota Composition Differs Between Children With β-Cell Autoimmunity and Those Without, 2013.
Martin-Dejardin, F. et al, Drug Delivery, A way to follow the viability of encapsulated Bifidobacterium bifidum subjected to a freeze-drying process in order to target the colon: Interest of flow cytometry, 2013.
Deshpande, A. et al, Industry, Diagnostic Testing for Clostridium difficile Infection in Patients With Inflammatory Bowel Disease, 2013.
Duboc, H. et al, GI Disease—General, Increase in fecal primary bile acids and dysbiosis in patients with diarrhea-predominant irritable bowel syndrome, 2012.
Duboc, H. et al, GI Disease—General, Connecting dysbiosis, bile-acid dysmetabolism and gut inflammation in inflammatory bowel diseases, 2013.
Durban, Ana et al, GI Disease—General, Structural alterations of faecal and mucosa-associated bacterial communities in irritable bowel syndrome, 2012.
Elliott, P.; Peakman, T., Industry, The UK Biobank sample handling and storage protocol for the collection, processing and archiving of human blood and urine, 2008.
Arumugam, M. et al, Analysis of Species in Feces, Enterotypes of the human gut microbiome, 2011.
Debast, S.; Bauer, M., Industry, European Society of Clinical Microbiology and Infectious Diseases (ESCMID): update of the treatment guidance document for Clostridium difficile infection (CDI), 2013.
Kootte, R. et al, Obesity Related, The therapeautic potential of manipulating gut microbiota in obesity and type 2 diabetes mellitus, 2012.
Fava, F.; Danese, S., GI Disease—General, Intestinal microbiota in inflammatory bowel disease: friend or foe?, 2011.
Marcille, J. (editor), FMT Studies and Reviews, Fecal Microbiota Transplantation for Treating Recurrent Clostridium difficile Infection, 2013.
Flores, R. et al, Analysis of Species in Feces, Assessment of the human faecal microbiota: II. Reproducibility and associations of 16S rRNA pyrosequences, 2012.
Vrieze, A. et al, FMT Studies and Reviews, Transfer of Intestinal Microbiota From Lean Donors Increases Insulin Sensitivity in Individuals With Metabolic Syndrome, 2012.
Vrieze, A. et al, FMT Studies and Reviews, Fecal transplant: A safe and sustainable clinical therapy for restoring intestinal microbial microbial balance in human disease?, 2013.
De Vrieze, Jop, FMT Studies and Reviews, The Promise of Poop, 2013.
Wasfy, M. et al, Microbial Preservation, Comparison of preservation media for storage of stool samples, 1995.
Weingarden, A. et al, FMT Studies and Reviews, Microbiota transplantation restores normal fecal bile acid composition in recurrent clostridium difficile infection, 2013.
Wenfeng, S. et al, Cryopreservation Studies, Appraising freeze-drying for storage of bacteria and their ready access in a rapid toxicity assessment assay, 2013.
Wu, N. et al, Cancer, Dysbiosis Signature of Fecal Microbiota in Colorectal Cancer Patients, 2013.

(56) References Cited

OTHER PUBLICATIONS

Wu, G.; Lewis, J., Microbiome papers, Analysis of the Human Gut Microbiome and Association With Disease, 2013.
Yoshimoto, S. et al, Obesity Related, Obesity-induced gut microbial metabolite promotes liver cancer through senescence secretome, 2013.
Zainah, H.; Silverman, A., Ulcerative Colitis, Fecal Bacteriotherapy: A Case Report in an Immunosuppressed Patient with Ulcerative Colitis and Recurrent Clostridium difficile Infection, 2012.
Zhang, F. et al, Chrohn's disease, Fecal microbiota transplantation for severe enterocolonic fistulizing Crohn's disease, 2013.
Ali, Shanom, Healthcare industry, Diverse sources of C. difficile infection, 2014.
Bakken, Johan et al, C Diff Studies, Treatment approaches including fecal microbiota transplantation for recurrent Clostridium difficile infection (RCDI) among infectious disease physicians, 2013.
Buffie, C.; Palmer, E., Microbiome papers, Microbiota-mediated colonization resistance against intestinal pathogens, 2013.
Cammarota, G. et al, FMT Studies and Reviews, Fecal Microbiota Transplantation for the Treatment of Clostridium difficile Infection A Systematic Review, 2014.
Cammarota, G. et al, FMT Studies and Reviews, Fecal transplantation for Colostridium difficile infection. Three cases treated in italy, 1993.
Clabots, C. et al, Strain typing, Development of a rapid and efficient restriction endonuclease analysis typing system for Clostridium difficile and correlation with other typing systems., 1993.
Crook, D. et al, C Diff Studies, Fidaxomicin versus vancomycin for Clostridium difficile infection: meta-analysisof pivotal randomized controlled trials, 2012.
De Leon et al, Ulcerative Colitis, Transient flare of ulcerative colitis after fecal microbiota transplantation for recurrent Clostridium difficile infection, 2013.
Downing, N. et al, Healthcare industry, Clinical Trial Evidence Supporting FDA Approval of Novel Therapeutic Agents, 2005-2012, 2014.
Dupont, H, Healthcare industry, Diagnosis and management of colostridium difficile infection, 2014.
Dutta, S.K. et al, FMT Studies and Reviews, Efficacy of Combined Jejunal and Colonic Fecal Microbiota Transplantation for Recurrent Clostridium difficile Infection, 2013.
Eyre, David et al, C Diff Studies, Diverse Sources of C. difficile Infection Identified on Whole-Genome Sequencing, 2013.
Friedman-Moraco, R.J. et al, FMT Studies and Reviews, Fecal Microbiota Transplantation for Refractory Clostridium difficile Colitis in Solid Organ Transplant Recipients, 2014.
Gomez-Simmons, A. et al, C Diff Studies, Comparison of 3 severity criteria for colostridium difficile infection, 2014.
Guillemin, I. et al, C Diff Studies, Patients' Experience and Perception of Hospital-Treated Clostridium difficile Infections: a Qualitative Study, 2014.
Gutierrez, R. et al, C Diff Studies, Epidemiology of Clostridium Difficile infection among active duty United States military personnel (1998-2010), 2013.
Jiang, z. et al, C Diff Studies, Physician Attitudes Toward the Use of Fecal Transplantation for Recurrent Clostridium difficile Infection in a Metropolitan Area, 2013.
Kahn, S. et al, Pediatrics, Colonoscopic fecal microbiota transplant for recurrent colostridium difficile infection in a child, 2012.
Kelly, Colleen, Healthcare industry, FDA's role in regulating FMT is imperative, 2013.
Killgore, G. et al, Strain typing, Comparison of Seven Techniques for Typing International Epidemic Strains of Clostridium difficile: Restriction Endonuclease Analysis, Pulsed-Field Gel Electrophoresis, PCR-Ribotyping, Multilocus Sequence Typing, Multilocus Variable-Number Tandem-Repeat Analysis, Amplified Fragment Length Polymorphism, and Surface Layer Protein A Gene Sequence Typing, 2008.
Knetsch, C.W. et al, Strain typing, Current application and future perspectives of molecular typing methods to study Clostridium difficile infections, 2013.
Kristjansson, M. et al, Strain typing, Comparison of Restriction Endonuclease Analysis, Ribotyping, and Pulsed-Field Gel Electrophoresis for Molecular Differentiation of Clostridium difficile Strains, 1994.
Gough, E., et al., "Systematic Review of Intestinal Microbiota Transplantation (Fecal Bacteriotherapy) for Recurrent Clostridium difficile Infection", (2011), 994-1002.
Barbut, F., et al., "Does a rapid diagnosis of Clostridium difficile infection impact on quality of patient management?", Clinical Microbiology and Infection, vol. 20, No. 2, Feb. 2014, 136-144.
Britton, R., et al., Role of the Intestinal Microbiota in Resistance to Colonization by Clostridium difficile, Gastroenterology (2014) (19 pgs.).
Chilton, C.H., et al., "Successful treatment of simulated Clostridum difficile infection in a human gut model by fidaxomicin first line and after vancomycin or metronidazole failure", J Antimicrob Chemother 2014; 69:451-462.
Duleba, K., et al., "Clostridium difficile infection in children hospitalized due to diarrhea", Eur. J. Clin. Microbiol. Infect. Dis. (2014) 33:201-209.
Keller, J.M., et al., "Clostridium difficile Infection in the Elderly", Clin. Geriatr Med 30 (2014) 79-93.
Mitchell, B. G., et al., "The prolongation of length of stay because of Clostridium difficile infection", American Journal of Infection Control 42 (2014) 164-7.
O'Horo, J.C., et al., "Treatment of recurrent Clostridium difficile infection: a systematic review", Infection (2014) 42:43-59.
Patel, L.N., et al., "Fecal transplantation therapy for Clostridium difficile—associated pouchitis", Int J Colorectal Dis (2014) 29:263-264.
Simon, M.S., "Cost-Effectiveness of Fidaxomicin for Clostridium difficile Treatment", Clinical Infectious Diseases, 2014; 58(4):603.
Bakken, J.S., "Fecal baceriotherapy for recurrent Clostridium difficile infection", Anaerobe 15 (2009) 285-289.
Kozak, G.K., et al., "Antimicrobial Resistance in *Escherichia coli* Isolates from Swine and Wild Small Mammals in the Proximity of Swine Farms and in Natural Environments in Ontario, Canada", Applied and Environmental Microbiology, Feb. 2009, p. 559-566.
Allen-Vercoe, Emma et al, C Diff Treatment with Fecal Transplant, A canadian working group report on fecal microbial therapy: microbial ecosystems therapeutics, 2012.
Kassam, Zain et al, C Diff Treatment with Fecal Transplant, Fecal transplant via retention enema for refractory or recurrent clostridium difficile infection, 2012.
Bennet, Justin et al, C Diff Treatment with Fecal Transplant, Treatment of ulcerative colitis by implantation of normal colonic flora, 1989.
Borody, TJ et al, Bowel disease treatment with FT, Bowel-flora alteration: a potential cure for inflammatory bowel disease and irritable bowel syndrome?, 1989.
Collins, Donald, Bowel disease treatment with FT, Pseudomembranous entercolitis—further observations on the value of donor fecal enemata as an adjunct in the treatment of pseudomembranous entercolitis, 1960.
Eiseman, B et al, Bowel disease treatment with FT, Fecal Enema as an adjuct in the treatment of pseudomembranous enterocolitis, 1958.
Paterson, David et al, Bowel disease treatment with FT, Putting back the bugs: bacterial treatment relieves chronic diarrhea, 1994.
Schwan, Anna et al, C Diff Treatment with Fecal Transplant, Relapsing clostridium difficile enterocolitis cure by rectal infusion of normal feces, 1984.
Bowden, Talmadge et al, Bowel disease treatment with FT, Pseudomembranous enterocolitis: mechanism of restoring floral homeostasis, 1981.
Tvede, M et al, C Diff Treatment with Fecal Transplant, Bacteriotherapy for chronic relapsing clostridium difficile diarrhea in six patients, 1989.

(56) References Cited

OTHER PUBLICATIONS

Berejnov, V. et al, Cryopreservation Studies, Effects of cryoprotectant concentration and cooling rate on vitrification of aqueous solutions, 2006.
Cody, William et al, Cryopreservation Studies, Skim milk enhances the preservation of thawed −80C bacterial stocks, 2008.
Hubalek, Zdenek, Cryopreservation Studies, Protectants used in the cryopreservation of microorganisms, 2002.
Van der Meulen, R. et al, Cryopreservation Studies, In vitro kinetic analysis of oligofructos consumption by bacteroides and bifidobacterium spp indicates different degredation mechanisms, 2006.
Falony, G et al, Cryopreservation Studies, Coculture fermentations of bifidobacterium species and bacteroides thetaiotaomicron reveal a mechanistic insight into the prebiotic effect of inulin-type fructans, 2009.
Carroll, I et al, Analysis of Species in Feces, Characterization of the fecal microbiota using high-throughput sequencing reveals a stable microbial community during storage, 2012.
Aslam, S et al, C Diff Studies, Treatment of clostridium difficile-associated disease: old therapies and new strategies, 2005.
Aas, J et al, C Diff Treatment with Fecal Transplant, Stool transplantation for older patients with clostridium difficile infection, 2009.
Mattila, E et al, C Diff Treatment with Fecal Transplant, Fecal transplantation, though colonoscopy, is effective therapy for recurrent clostridium difficile infection, 2012.
Arkkila, P. E., C Diff Treatment with Fecal Transplant, Fecal bacteriotherapy for recurrent clostridium difficile infection, 2011.
Borody, TJ et al, Bowel disease treatment with FT, Treatment of ulcerative colitis using fecal bacteriotherapy, 2003.
Borody, TJ et al, C Diff Treatment with Fecal Transplant, Bacteriotherapy using fecal flora, 2004.
Curtin, Ciara, Analysis of Species in Feces, Researchers examine the genetic diversity of the human gut microbiome, 2012.
Petrof, Khoruts, Microbiome papers, From Stool Transplants to Next-generation Microbiota Therapeutics, 2014.
Brandt, L et al, C Diff Treatment with Fecal Transplant, Long-term follow-up of colonoscopic fecal microbiota transplant for recurrent clostridium difficile infection (paper and question/answer with Brandt), 2012.
Rolfe, R et al, Analysis of Species in Feces, Bacterial interference between clostridium difficile and normal fecal flora, 1981.
Gewolb, Ira et al, Analysis of Species in Feces, Stool microflora in extremely low birthweight infants, 1999.
Eyre, David et al, C Diff Studies, Predictors of first recurrence of clostridium difficile infection: implications for initial management, 2012.
Brandt, L et al, C Diff Treatment with Fecal Transplant, American journal of gastroenterology lecture: intestinal microbiota and the role of fecal microbiota transplant (FMT) in treatment of c diff infection, 2012.
Kassam, Zain et al, C Diff Treatment with Fecal Transplant, Fecal microbiotia transplantation for clostridium difficile infection: systematic review and meta-analysis, 2013.
Eckburg, Paul B. et al, Analysis of Species in Feces, Diversity of the Human Intestinal Microbial Flora, 2005.
Tedeschi, Rosamaria; De Paoli, Paolo, Bacterial Preservation via Freezing, Collection and Preservation of Microorganisms, 2011.
Bell, Caitlin H, Centrifugation, The Effects of Centrifugation and Filtration as Pre-Treatments in Bacterial Retention Studies, 2005.
Hao, W.; Lee, Y., Microbiome papers, Microflora of the Gastrointestinal Tract, 2004.
Peterson, B et al, Centrifugation, Bacterial Cell Surface Damage due to Centrifugal Compaction, 2012.
Hamilton, Matthew et al, Bacterial Preservation via Freezing, High-throughput DNA Sequence Analysis Reveals a Stable Engraftment of Gut Microbiota Following Transplantation of Previously Frozen Fecal Bacteria, 2013.

Burke, Kristin et al, C Diff Treatment with Fecal Transplant, Fecal Transplantation for recurrent colostridium difficile infection in older adults: a review, 2013.
Ananthakrishnan, A. et al, GI Disease—General, Genetic risk factors for Colostridium difficile infection in ulcertive colitis, 2013.
Bonfrate, Leonilde et al, GI Disease—General, Microbiota in health and irritable bowel syndrome: current knowledge, perspectives and therapeutic options, 2013.
Dey, Neelendu et al, GI—General, Association of gut microbiota with post-operative clinical course in Crohn's disease, 2013.
Brahe, L.K. and Larson, L.H., Obesity Related, Is butyrate the link between diet, intestinal microbiota and obesity-related metabolic diseases?, 2013.
Guerrero, D.M. et al, C-Diff Studies, Asymptomatic carriage of toxigenic Clostridium difficile by hospitalized patients, 2013.
Durban, Ana et al, GI Disease—General, Instability of the faecal microbiota in diarrhoea-predominant irritable bowel syndrome, 2013.
Jakobsson, Hedvig et al, Gut Microbiome News, Decreased gut microbiota diversity, delayed Bacteroidetes colonisation and reduced Th1 responses in infants delivered by Caesarean section, 2013.
Lee, S.M. et al, Gut Microbiome News, Bacterial colonization factors control specificity and stability of the gut microbiota, 2013.
Hoffmann, Christian et al, Analysis of Species in Feces, Archaea and Fungi of the Human Gut Microbiome: Correlations with Diet and Bacterial Residents, 2013.
Multiple articles, Agar Plate Info, Anaerobic Bacteriology, 2007.
Abubaker, I et al, Microbiome papers, Health Technology Assessment 2007 vol. 11 No. 36, 2007.
Ott, Stephen et al, Analysis of Species in Feces, Quantification of Intestinal Bacterial Populations by Real-Time PCR with a Universal Primer Set and Minor Groove Binder Probes: A Global Approach to the Enteric Flora, 2004.
Kump, Patrizia, et al, Ulcerative Colitis, Alteration of intestinal dysbiosis by fecal microbiota transplantation does not induce in remission in patients with chronic active uncerative colitis, 2013.
Shwartz, Margot et al, C-Diff Treatment with Fecal Transplant, Norovirus Gastroenteritis After Fecal Microbiota Transplantation for Treatment of Colostridium Difficile Infection Despite Asymptonatic Donors and Lack of Sick Contacts, 2013.
Brandt, Lawrence, C-Diff Treatment with Fecal Transplant, Norovirus Gastroenteritis After Fecal Microbiota Transplantation for Treatment of Colostridium Difficile Infection Despite Asymptonatic Donors and Lack of Sick Contacts, 2013.
Allen, Stephen et al, Drug Delivery, Lactobacilli and bifidobacteria in the prevention of antibiotic-associated diarrhea and clostridium difficile diarrhea in older inpatients (PLACIDE): a randomized, double-blind, placebo-controlled, multicentre trial, 2013.
Varum, F.J.O. et al, Drug Delivery, A novel coating concept for ileo-colonic drug targeting: Proof of concept in humans using scintigraphy, 2013.
Huang, Y et al, Drug Delivery, A novel plug-controlled colon-specific pulsatile capsule with tablet of curcumin-loaded SMEDDS, 2013.
Chavarri, Maria et al, Drug Delivery, Microencapsulation of a probiotic and prebiotic in alginate-chitosan capsules improves survival in simulated gastro-intestinal conditions, 2010.
Adams, Stephen, et al, Ulcerative Colitis, Ulcerative Colitis, 2013.
Baron, Todd, C Diff Treatment with Fecal Transplant, Fecal Microbiota Transplant: We know its history, but can we predict its future?, 2013.
Vyas, D et al, C Diff Treatment with Fecal Transplant, Stool therapy may become a preferred treatment of recurrent Colostridium difficile, 2013.
Karadsheh, Z.; Sule, S., C Diff Treatment with Fecal Transplant, Fecal transplantation for the treatment of recurrent colostridium difficile infection, 2013.
Brandt, Lawrence; Aroniadis, Olga, C Diff Treatment with Fecal Transplant, An overview of fecal microbiota transplantation: techniques, indications and outcomes, 2013.

(56) References Cited

OTHER PUBLICATIONS

Weir, T. et al, Analysis of Species in Feces, Stool microbiome and metabolome differences between colorectal cancer patients and healthy adults, 2013.
Navidad, J. et al, Donor Screening, Evaluation of Luminex xTAG gastrointestinal pathogen analyte specific reagents for high throughput, simultaneous detection of bacteria, viruses, and parasites of clinical and public health importance, 2013.
Ridlon, J.M. et al, Microbiome papers, Cirrhosis, bile acids and gut microbiota. Unraveling a complex relationship, 2013.
Vujkovic-Cvijin, I. et al, Microbiome papers, Dysbiosis of the Gut Microbiota Is Associated with HIV Disease Progression and Tryptophan Catabolism, 2013.
Minot, S. et al, Analysis of Species in Feces, Rapid evolution of the gut virome, 2013.
Atarashi, K. et al, Analysis of Species in Feces, Treg introduction by a rationally selected mixture of colostrudia strains from the human microbiota, 2013.
Martinez, I. et al, Microbiome papers, Long-term temporal analysis of the human fecal microbiota revealed a stable core of dominant bacterial species, 2013.
Collins, S. et al, Microbiome papers, The adoptive transfer of behavioral phenotype via the intestinal microbiota: experimental evidence and clinical implications, 2013.
Borody, TJ et al, C Diff Treatment with Fecal Transplant, Fecal microbiota transplantation: Indications, methods, evidence, and future directions, 2013.
Van den Abbeele, P. et al, Microbiome papers, Prebiotics, fecal transplants and microbial network units to stimulate biodiversity of the human gut microbiome, 2013.
Van Nood, E. et al, C Diff Treatment with Fecal Transplant, Duodenal infusion of donor feces for recurrent colostridium difficile, 2013.
Manges, A. et al, Microbiome papers, Comparative metagenomic study of alterations to the intestinal microbiota and risk of nosocomial colostridium difficile-associated disease, 2010.
Fox, Jeffery, General FMT News and Regulations, Fecal transplants to follow FDA rules, 2013.
Chitnis, A. et al, C Diff Studies, Epidemiology of community-associated colostridium difficile infection, 2009 through 2011, 2013.
Alonso, Carolyn; Marr, Kieren, C Diff Studies, Colostridium difficile infection among hematopoietic stem cell transplant recipients: beyond colitis, 2013.
Burnham, Carey-Ann; Carroll, Karen, C Diff studies, Diagnosis of colostridium difficile infection: an ongoing conundrum for clinicians and clinical laboratories, 2013.
Brecher, S. et al, C Diff Studies, Laboratory diagnosis of colostridium difficile infections: a practical guide for clinicians: there is a light at the end of the colon, 2013.
Onneby, K. et al, Cryopreservation Studies, Effects of di- and polusaccharide formulations and storage conditions on survival of freeze-dried sphingobium, 2013.
Tsai, S. et al, Drug Delivery, Hyaluronan-cisplatin conjugate nanoparticles embedded in Eudragit S100-coated pectin/alginate microbeads for colon drug delivery, 2013.
Gupta, A. et al, Drug Delivery, Design and development of liposomes for colon targeted drug delivery, 2013.
Xu, Q. et al, Drug Delivery, KGM and PMAA based pH-sensitive interpenetrating polymer network hydrogel for controlled drug release, 2013.
Dixon, E. et al, Counting Bacteria, Solid-phase microextraction and the human fecal VOC metabolome, 2011.
Kassam, Zain et al, Donor Screening, Navigating long-term safety in fecal microbiota transplantation, 2013.
El-Matary, Wael, Donor Screening, Fecal Microbiots Transplantation: Long-Term Safety Issues, 2013.
Hoover, D; Rodriguez-Palacios, A., C Diff Studies, Transmission of colostridium difficile in foods, 2013.
Halabi, W. et al, C Diff Studies, Colostridium Difficile colitis in the united states: a decade of trends, outcomes, risk factors for colectomy, and mortality after colectomy, 2013.
Davidovics, Z.; Sylvester, F., Ulceratice Colitis, Medical Stool: The Future Treatment for Inflammatory Bowl Disease?, 2013.
Barletta, J. et al, Intestinal pH, Proton pump inhibitors and the risk for hospital aquired colostridium difficile infection, 2013.
Kim, B. et al, Microbiome papers, Current status and future promise of the human microbiome, 2013.
Owens, C. et al, Donor Screening, Fecal microbiota transplantation and donor standardization, 2013.
Ridaura, V. et al, Obesity Related, Gut microbiota from twins discordant for obesity modulate metabolism in mice, 2013.
Shim, J., GI Disease—General, Gut microbiota in inflammatory bowel disease, 2013.
Zhao, L. et al, Microbiome papers, Targeting the human genome—microbiome axis for drug discovery: inspirations from global systems biology and traditional chinese medicine, 2013.
Viswanathan, VK, Microbiome papers, The meddling microbes midst our medicines, 2013.
Olle, Bernat, Microbiome papers, Medicines from microbiota, 2013.
Konkel, Lindsey, Microbiome papers, The environment within: exploring the role of the gut microbiome in health and disease, 2013.
Lichtman, J. et al, Microbiome papers, Host-centric proteomics of stool: a novel strategy focused on intestinal responses to the gut microbiota, 2013.
Klein, E.J., et al., "Diarrhea Etiology in a Children's Hospital Emergency Department: A Prospective Cohort Study", Clin Infect Dis., Oct. 1, 2006; 43(7):807-13.
Korpela, K., et al., "Gut microbiota signatures predict host and microbiota responses to dietary interventions in obese individuals", PLOS One, Mar. 2014, vol. 9, Issue 3, e90702 (10 pgs.).
Larson, H.E., et al., "Epidemiology of Clostridium difficile in infants", J Infect Dis., Dec. 1982; 146(6):727-33.
Lawley, T.D., et al., "Intestinal colonization resistance", Immunology, Jan. 2013; 138(1):1-11.
Lee, C., et al., "The outcome and long-term follow-up of 94 patients with recurrent and refractory Clostridium difficile infection using single to multiple fecal microbiota transplantation via retention enema", Eur J. Clin Microbiol Infect Dis., Mar. 14, 2014 (4 pgs.).
Ley, R., "The sweet tooth of Clostridium difficile", Nature Medicine, vol. 20, No. 3, Mar. 2014, 248-49.
Lofland, D., et al., "Fecal Transplant for Recurrent Clostridium difficile Infection", Clin Lab Sci., 2013, 26(3):131-5.
Lopetuso, L.R., et al., "Commensal Clostridia: leading players in the maintenance of gut hemostasis", Gut Pathogens, 2013, 5:23 (8 pgs.).
Lucado, J., et al., "Clostridium difficile Infections (CDI) in Hospital Stays, 2009", HCUP Statistical Brief #124, Jan. 2012. Agency for Healthcare Research and Quality, Rockville, MD http:www.hcup-us.ahrg.gove/reports/statbriefs/sb124.pdf, pp. 1-12.
Martin, J., et al., "Clostridium difficile: biological therapies", Curr Opin Infect Dis., Oct. 2013; 26(5):454-60.
Martinez, J.A., et al., "Role of dietary polyphenols and inflammatory processes on disease progression mediated by the gut microbiota", Rejuvenation Res., Oct. 2013; 16(5):435-7.
McCune, V.L., et al., "Faecal transplantation for the treatment of Clostridium difficile infecton: a review", Int J Antimicrob Agents, Mar. 2014; 43(3):201-6.
Mellow, M.H., et al., "Colonscopic Fecal Bacteriotherapy in the Treatment of Recurrent Clostridium Difficile Infection—Results and Follow-up", OSMA Journal, Mar. 2011, pp. 89-91.
Mitchell, M., "Determining Criticality-Process Parameters and Quality Attributes Part I: Criticality as a Continum", BioPharam, Dec. 1, 2013, (7 pgs.).
Mitchell, M., "Determining Criticality-Process Parameters and Quality Attributes Part II; Design of Experiments and Data-Driver Criticality", BioPharam, Jan. 1, 2014, (9 pgs.).
Moayyedi, P., et al., "Canadian Association of Gastroenterology position statement: Fecal microbiota transplant therapy", Can J Gastroeneterol Hepatol, vol. 28, No. 2, Feb. 2014 (3 pgs.).

(56) References Cited

OTHER PUBLICATIONS

Nagaro, K.J., et al., "Non-Toxigenic Clostridium difficile Protects Hamsters Against Challenge with Historic and Epidemic Toxigenic BI/NAP1/027 C. difficile", Antimicrob Agens Chemother. Nov. 2013; 57(11):5266-70.

Numata, K., et al., "Silk-based delivery systems of bioactive molecules", Adv Drug Deily Rev. Dec. 30, 2010; 62(15):1497-1508.

Nylund, C.M., et al., "Clostridium difficile Infection in Hospitalized Children in the United States", Arch Pediatr Adolesc Med 2011;165(5):451-457.

Ohkusu, K., et al., "Cost-Effective and Rapid Presumptive Identification of Gram-Negative Bacilli in Routine Urine, Pus, and Stool Cultures: Evaluation of the Use of CHROMagar Orientation Medium in Conjunction with Simple Biochemical Tests", Journal of Clinical Microbiology, Dec. 2000, vol. 38, No. 12, p. 4586-4592.

Oldfield, E.C., et al., "Clinical update for the diagnosis and treatment of Clostridium difficile infection", World J Gastrointest Pharacol Ther, Feb. 6, 2014; 5(1):1-26.

Parekh, P.J., et al., "The role and influence of gut microbiota in pathogenesis and management of obesity and metabolic syndrome", Front Endocrinol (Lausanne), Apr. 7, 2014; 5:47 (7 pgs.).

Pascarella, F., et al., "Impact of Clostridium difficile infection on pediatric inflammatory bowel disease", J Pediatr. Jun. 2009; 154(6):854-8.

Perez-Chanona, E., et al., "From promotion to management: The wide impact of bacteria on cancer and its treatment", Bioessays, Apr. 22, 2014 (7 pgs.).

Pierce, K., "Physician Induced CRE Infections", 2014, Hardy Diagnostics (4 pgs.).

Planche, T.D., et al., "Differences in Outcome According to Clostridium difficile Testing Method: A Prospective Multicentre Diagnostic Validation Study of C difficile Infection", Lancet Infect Dis. Nov. 2013; 13(11):936-45.

Preheim, S.P., et al., "Computational Methods for High-Throughput Comparative Analyses of Natural Microbial Communities", Methods Enzymol. 2013; 531:354-70.

Qa'Dan, M., et al., "pH-induced conformational changes in Clostridium difficile toxin B", Infect Immun., May 2000; 68(5):2470-4.

Rao, A., et al., "In Vitro Killing of Nosocomial Pathogens by Acid and Acidified Nitrite", Antimicrob. Agents Chemother. 2006, 50(11):3901-3904.

Ringel, Y., et al., "The Intestinal Microbiota and Immune Function in the Pathogenesis of Irritable Bowel Syndrome", Am J Physiol Gastrointest Liver Physiol, Oct. 15, 2013; 305(8):G529-41.

Rogler, G., et al., "The heart and the gut", Eur Heart J, Feb. 2014; 35(7):426-30.

Rohlke, F., et al., "Fecal microbiota transplantation in relapsing Colostridium difficile infection", Therap Adv Gastroenterol., Nov. 2012; 5(6):403-20.

Rubin, T.A., et al., "Fecal microbiome transplantation for recurrent Clostridium difficile infection: Report on a case series", Anaerobe 19 (2013) 22-26.

Safdar, N., "Clostridium difficile: The Emerging Epidemic", Mayo Clinic Proceedings, Nov. 2012, vol. 87, No. 11, 1037-1039.

Sandora, T.J., et al., "Epidemiology and risk factors for Clostridium difficile infection in children", Pediatr Infect Dis J, Jul. 2011; 30(7):580-4.

Schwartz, K., et al., "Severe clinical outcome is uncommon in Clostridium difficile infection in children: a retrospective cohort study", BMC Pediatr, Jan. 31, 2014; 14:28 (6 pgs.).

See, I., et al., "NAP1 Strain Type Predicts Outcome From Clostridium difficile Infection", Clin Infect Dis, May 2014; 58(10):1394-400.

Senior, K., "Faecal transplantation for recurrent C difficile diarrhoea", Lancet Infect Dis., Mar. 2013; 13(3):200-1.

Sha, S. et al., "Systematic review: faecal microbiota transplantation therapy for digestive and nondigestive disorders in adults and children", Aliment Pharmacol Ther, May 2014; 39(10):1003-32.

Shaughnessy, M.K., et al., "Unnecessary Antimicrobial Use in Patients With Current or Recent Clostridium difficile Infection", Infect Control Hosp Epidemiol 2013;34(2):109-116.

Smith, M.B., et al., "Policy: How to regulate faecal transplants", Nature, Feb. 20, 2014; 506(7488):290-1.

Sofi, A., et al., "Physician outlook toward fecal microbiota transplantation in the treatment of Clostridium difficile infection", Am J Gastroenterol, Oct. 2013; 108(10):1661-2.

Solari, P., et al., "Tempered enthusiasm for Fecal transplantation", Clin Infect Dis, Apr. 23, 2014 (3 pgs.).

Stahlmann, J., et al., "Detection of nosocomial Clostridium difficile infections with toxigenic strains despite negative toxin A/B testing on stool samples", Clin Microbiol Infect, Jan. 23, 2014 (10 pgs.).

Stock, J., "Gut microbiota: an environmental risk factor for cardiovascular disease", Atherosclerosis, Aug. 2013; 229(2):440-2.

Sunkesula, V.C., et al., "Does empirical Clostridium difficile infection (CDI) therapy result in false-negative CDI diagnostic test results?", Clin Infect Dis, Aug. 2013; 57(4):494-500.

Suvarna, K., et al., "Case Studies of Microbial Contamination in Biologic Product Manufacturing", Microbiology, Jan./Feb. 2011, pp. 50-57.

Tang, P., et al, "Limited clinical utility of Clostridium difficile toxin testing in infants in a pediatric hospital", Diagn Microbiol Infect Dis, Jun. 2005; 52(2):91-4.

Taori, S.K., et al., "A prospective study of community-associated Clostridium difficile infections: The role of antibiotics and co-infections", J Infect, Apr. 26, 2014 (11 pgs.).

Taur, Y., et al., "Harnessing microbiota to kill a pathogen: Fixing the microbiota to treat Clostridium difficile infections", Nat Med., Mar. 2014; 20(3):246-7.

Adler, A., et al., "Trends and Changes in Clostridium difficile Diagnostic Profiles and Their Impact on the Proportion of Positive Samples: a National Survey", Clin. Microbiol Infect. Mar. 27, 2014, 10.1111/1469-0691.12634.

Aronoff, D.M., "Host-Pathogen Interactions in Clostridium difficile Infection: It Takes Two to Tango", Clin Infect Dis. (2014) 58 (10):1401-1403.

Arvand, M., et al., "Increased incidence of Clostridium difficile PCR ribotype 027 in Hesse, Germany, 2011 to 2013", Euro Surveill, 2014:19(10) 1-6.

Aspevall, O., et al., "Performance of Four Chromogenic Urine Culture Media after One or Two Days of Incubation Compared with Reference Media", Journal of Clinical Microbiology, vol. 40, No. 4, Apr. 2002, 1500-1503.

ASTM International, "Standard Practice for Climatic Stressing of Packaging Systems for Single Parcel Delivery", Book of Standards vol. 15.10, 2010, 10.1520/F2825-10E01 (3 pgs.).

Austin, M., et al., "Fecal Microbiota Transplantation in the Treatment of Clostridium difficile Infections", The American Journal of Medicine (2014), doi: 10.1016/j.amjmed.2014.02.017 (15 pgs.).

Bakken, J., et al., "Treating Clostridium difficile Infection With Fecal Microbiota Transplantation", Clinical Gastroenterology and Hepatology 2011;9:1044-1049.

Bartlett, J., "A Call to Arms: The Imperative for Antimicrobial Stewardship", CID, 2011:53 (Suppl 1) S4-S7.

Bennett, P.S., et al., "What Nurses Need to Know About Fecal Microbiota Transplantation: Education, Assessment, and Care for Children and Young Adults", J. Pediatr Nurs., Feb. 7, 2014, doi: 10.1016/j.pedn.2014.01.013 (8 pgs.).

Boenning, D.A., et al., "Clostridium difficile in a pediatric outpatient population", Pediatric Infectious Disease, vol. 1, No. 5, 336-338.

Boone, J.H., et al., "Clostridium difficile prevalence rates in a large healthcare system stratified according to patient population, age, gender, and specimen consistency", Eur J Clin Microbiol Infect Dis (2012) 31:1551-1559.

Brace, C., et al., "Microbial composition analysis of Clostridium difficile infections in an ulcerative colitis patient treated with multiple fecal microbiota transplantations", J Crohns Colitis (2014), http://dx.doi.org/10.1016/j.crohns.2014.01.020 (5 pgs.).

Cammarota, G., et al., "Gut microbiota modulation: probiotics, antibiotics or fecal microbiota transplantation?" Intern Emerg Med (2014), DOI: 10.1007/s11739-014-069-4 (9 pgs.).

(56) References Cited

OTHER PUBLICATIONS

CDC, "Vital Signs: Preventing Clostridium difficile Infections", MMWR, Mar. 9, 2012, vol. 61, No. 9, 157-162.
Chisti, Y., "Hydrodynamic Damage to Animal Cells", Critical Reviews in Biotechnology, 21(2):67-110 (2001).
Cohen, S.H., et al., "Clinical Practice Guidelines for Clostridium difficile Infection in Adults: 2010 Update by the Society for Healthcare Epidemiology of America (SHEA) and the Infectious Diseases Society of America (IDSA)", Infection Control and Hospital Epidemiology, vol. 31, No. 5 (May 2010), pp. 431-455.
Coteur, G., et al., "Evaluation of the meaningfulness of health-related quality of life improvements as assessed by the SF-36 and the EQ-5D VAS in patients with active Crohn's disease", Aliment Pharmacol Ther 29, (2009) 2032-1041.
D'Agostino, R.B., et al., "Risk Estimation for Recurrent Clostridium Difficile Infection Based on Clinical Factors", Clin. Infect Dis May 2014; 58(10):1386-93.
Dallas, K.B., et al., "Life after colectomy for fulminant Clostridium difficile colitis: a 7-year follow up study", The American Journal of Surgery (2014) 207, 533-539.
Deweerdt, S., "A complicated relationship status", Nature, Apr. 17, 2014; 508(7496):S61-3.
Ding, T., et al., "Dynamics and associations of microbial community types across the human body", Nature, May 15, 2014; 509(7500):357-60.
Dominguez, S.R., et al., "High Colonization Rate and Prolonged Shedding of Clostridium difficile in Pediatric Oncology Patients", Clin Infect Dis, Apr. 29, 2014 (11 pgs.).
Dubberke, E.R., et al., "Burden of Clostridium difficile on the Healthcare System", CID 2012:55 (Suppl 2), S88-S92.
Dubberke, E., "Clostridium Difficile Infection: The Scope of the Problem", Journal of Hospital Medicine, vol. 7, Supp. 3, Mar. 2012, S1-S4.
Dupont, H.L., "Review article: evidence for the role of gut microbiota in irritable bowel syndrome and its potential influence on therapeutic targets", Aliment Pharmacol Ther, May 2014; 39(10):1033-42.
Ehlermann, P., et al., "Donor fecal transfer for recurrent Clostridium difficile-associated diarrhea in heart transplantation", The Journal of Heart and Lung Transplantation, vol. 33, No. 5, May 2014, 551-553.
El Feghaly, R.E., et al., "Markers of Intestinal Inflammation, Not Bacerial Burden, Correlate With Clinical Outcomes in Clostridium difficile Infection", Clin Infect Dis. Jun. 2013; 56(12):1713-21.
Elixhauser, A., et al., "Readmissions following Hospitalizations with Clostridium difficile Infections, 2009", HCUP Statisical Brief #145, Dec. 2012, Agency for Healthcare Research and Quality, Rockville, MD, pp. 1-11.
Food and Drug Administration, "Small Business Guide to FDA", 2011 (28 pgs.).
Fridkin, S., et al., "Vital Signs: Improving Antibiotic Use Among Hospitalized Patients", MMWR, Mar. 7, 2014, vol. 63, No. 9, 194-200.
Gerding, D.N., "Global Epidemiology of Clostridium difficile Infection in 2010", Infection Control and Hospital Epidemiology, 2010, vol. 31, No. S1, pp. S32,S34.
Guarner, J., et al., "Correlation of the detection of Clostridium difficile toxins in stools and presence of the clostridia in tissues of children", Human Pathology (2010) 41, 1586-1592.
Guo, B., et al., "Systematic review: faecal transplantation for the treatment of Clostridium difficile-associated disease", Aliment Pharmacol. Ther. 2012; 35:865-875.
Gupta, A., et al., "Community-acquired Clostridium difficile infection: an increasing public health threat", Infection and Drug Resistance 2014:7 63-72.
Harpe, S.E., et al., "Characterization of Continued Antibacterial Therapy After Diagnosis of Hospital-Onset Clostridium difficile Infection: Implications for Antimicrobial Stewardship", Pharmacotherapy, vol. 32, No. 8, 2012, pp. 744-754.
Hawes, R.H., et al., "A concensus document on bowel preparation before colonoscopy: Prepared by a Task Force From The American Society of Colon and Rectal Surgeons (ASCRS), the American Society for Gastrointestinal Endoscopy (ASGE), and the Society of American Gastrointestinal and Endoscopic Surgeons (SAGES)", Gastrointestinal Endoscopy, vol. 63, No. 7, 2006, 894-910.
Hennequin, C., et al., "GroEL (Hsp60) of Clostridium difficile is involved in cell adherence", Microbiology (2001), 147, 87-96.
Hensgen, M.P.M., et al., "Time interval of increased risk for Clostrium difficile infection after exposure to antibiotics", J Antimicrob Chemother 2012; 67:742-748.
Hourigan, S.K., et al., "The Prevalence of Clostridium difficile Infection in Pediatric and Adults Patients with Inflammatory Bowel Disease", Dig Dis Sci May 1, 2014, DOI: 10.1007/s10620-0143169-4 (6 pgs.).
Hu, M.Y., et al., "Prospective Derivation and Validation of a Clinical Prediction Rule for Recurrent Clostridium difficile Infection", Gastroenterology 2009; 136:1206-1214.
Humphreys, D.P., et al., "Antibodies for the treatment of Clostridium difficile infection", Clin Vaccine Immunol. Apr. 30, 2014, doi:10.1128/CV1.00116-14 (35 pgs.).
Johnson, S. et al., "Fidaxomicin "Chaser" Regimen Following Vancomycin for Patients With Multiple Clostridium difficile Recurrences", Clin Infect Dis. Jan. 2013; 56(2):309-10.
Jones, A.M., et al., "Clostridium difficile: A European perspective", J Infect (2012), http://dx.doi.org/10.1016/j.jinf.2012.10.019, pp. 1-14.
Kahn, S.A., et al., "Colonscopic Fecal Microbiota Transplant for Recurrent Clostridium difficile Infection in a Child", The American Journal of Gastroenterology, vol. 107, Dec. 2012, 1930-1931.
Kahn, S.A., et al., "Fecal Bacteriotherapy for Ulcerative Colitis: Patients Are Ready, Are We?", Inflamm Bowel Dis. Apr. 2012; 18(4):676-684.
Kao, D., et al., "Fecal Microbiota Transplantation Inducing Remission in Crohn's Colitis and the Associated Changes in Fecal Microbial Profile", J Clin Gastroenterol, 2014, PMID: 24667590 (4 pgs.).
Kassam, Z., et al., "Fecal Microbiota Transplantation for Clostridium difficile Infection: Systematic Review and Meta-Analysis", Am J Gastroenterol Mar. 19, 2013; doi:10.1038/ajg.2013.59, pp. 1-9.
Khanna, S., et al., "Clostridium difficile infection: management strategies for a difficult disease", Ther Adv Gastroenterol 2014, vol. 7(2) 72-86.
Kim, J., et al., "Epidemiological Features of Clostridium difficile-Associated Disease Among Inpatients at Children's Hospitals in the United States, 2001-2006", Pediatrics 2008; 122:1266-1270.
Kim, J., "Editorial Commentary: 'High Colonization Rate and Prolonged Shedding of Clostridium difficile in Pediatric Oncology Patients'", Clinical Infectious Diseases Advance Access, 2014 (6 pgs.).
Taur, Y., et al., "Intestinal domination and the risk of bacteremia in patients undergoing allogeneic hematopoietic stem cell transplantation", Clin Infect Dis., Oct. 2012; 55(7):905-14.
Tickler, I.A., et al., "Strain Types and Antimicrobial Resistance Patterns of Clostridium difficile Isolates from the United States: 2011-2013", Antimicrob Agents Chemother, Apr. 21, 2014 (17 pgs.).
Tran, M.C., et al., "Therapy of Clostridium difficile infection: perspectives on a changing paradigm", Expert Opin Pharmacother., Dec. 2013; 14(17):2375-86.
Tshudin-Sutter, S., et al., "Clostridium difficile: novel insights on an incessantly challenging disease", Curr Opin Infect Dis., Aug. 2012; 25(4):405-11.
Tyler, A., et al., "Analyzing the Human Microbiome: A 'How To' guide for Physicians", Am J Gastroenterol, Apr. 22, 2014 (11 pgs.).
Udayappan, S.D., et al., "Intestinal microbiota and fecal transplantation as treatment modality for insulin resistance and type 2 diabetes mellitus", Clin Exp Immunol., Feb. 15, 2014 (17 pgs.).
Vaarala, O., "Human intestinal microbiota and type 1 diabetes", Curr Diab Rep., Oct. 2013; 13(5):601-7.
Vaishnavi, C., "Fecal microbiota transplantation for management of Clostridium difficile infection", Indian J Gastroenterol, Apr. 20, 2014 (7 pgs.).

(56) References Cited

OTHER PUBLICATIONS

Van der Wilden, G., et al., "Fulminant Clostridium difficile colitis: Prospective development of a risk scoring system", J Trauam Actue Care Surg., vol. 76, No. 2, 2014, 424-30.
van Nood, E., et al., "Struggling with Recurrent Clostridium difficile Infections: Is Donor Faeces the Solution?", Euro Surveill. 2009;14(34), pp. 1-6.
Vandenplas, Y., et al., "Fecal Microbial Transplantation in a One-Year-Old Girl with Early Onset Colitis—Caution Advised", J Pediatr Gastroenterol Nutr., Jan. 2, 2014 (11 pgs.).
Varkonyi, I., et al., "Findings of a hospital surveillance-based outcome evaluation study for Clostridium difficile-associated colitis", Clin Microbiol. Infect., Apr. 28, 2014 (18 pgs.).
Vartoukian, S., et al., "Strategies for culture of 'unculturable' bacteria", FEMS Microbiol Lett 309 (2010) 1-7.
Vincent, C., et al., "Reductions in intestinal Clostridiales precede the development of nosocomial Clostridium difficile infection", Microbiome, 2013, 1:18 (11 pgs.).
Wang, W., et al., "Low Vitamin D Level is an Independent Predictor of Poor Outcomes in Clostridium difficile—Associated Diarrhea", Ther Adv Gastroenterol., 2014; 7(1):14-19.
Wendt, J. M., et al., "Clostridium difficile Infection Among Children Across Diverse US Geographic Locations", Pediatrics, vol. 133, No. 4, Apr. 2014 (10 pgs.).
Wiegand, P.N., et al., "Clinical and economic burden of Clostridium difficile infection in Europe: a systematic review of healthcare-facility-acquired infection", Journal of Hospital Infection 81 (2012) 1-14.
Youngster, I., et al., "Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014; 58(11):1515-22.
Youngster, I., et al., "Supplementary Appendix: Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014 (6 pgs.).
Zilberberg, M.D., et al., "Clostridium difficile Infections among Hospitalized Children, United States, 1997-2006", Emerging Infectious Diseases, vol. 16, No. 4, Apr. 2010, 604-609.
Zilberberg, M.D., et al., "Development and Validation of a Recurrent Clostridium difficile Risk-Prediction Model", Journal of Hospital Medicine, Apr. 4, 2014 (6 pgs.).
Zimmer, C., "Bacterial Ecosystems Divide People Into 3 Groups, Scientists Say", The New York Times, Apr. 20, 2011 (4 pgs.).
Canadian Notice of Allowance dated Jun. 5, 2015, Application No. 2,788,558, 1 pg.

* cited by examiner

BACTERIOTHERAPY FOR CLOSTRIDIUM DIFFICILE COLITIS

CLAIM OF PRIORITY

This application is a U.S. National Stage Filing under 35 U.S.C. 371 of International Patent Application Serial No. PCT/US2011/000184, filed Feb. 1, 2011, and published on Aug. 4, 2011 as WO 2011/094027, which claims the benefit of priority under 35 U.S.C. 119(e) to Hlavka U.S. Provisional Patent Application Ser. No. 61/337,283, entitled "BACERIOTHERAPY FOR *CLOSTRIDIUM DIFFICILE* COLITIS," filed on Feb. 1, 2010, and to Hlavka U.S. Provisional Patent Application Ser. No. 61/351,184, entitled "BACERIOTHERAPY FOR *CLOSTRIDIUM DIFFICILE* COLITIS," filed on Jun. 3, 2010, each of which is hereby incorporated by reference in its entirety.

BACKGROUND

Between 300 and 1000 different species of bacteria reside in a healthy gastrointestinal (GI) tract. Clostridia are anaerobic, spore-forming bacteria. Certain species of *clostridium* are pathogens, producing toxins that can be harmful to humans. *Clostridium difficile* ("C. diff") is one species of *clostridium* that, if overpopulated in the GI tract, can release toxins that can cause a number of symptoms, including bloating, constipation, diarrhea, inflammation, abdominal pain, among others that, in certain cases, can lead to death.

When stressed, *clostridium difficile* create spores that can tolerate extreme conditions many active bacteria cannot. Generally, clostridia do not compete well in a healthy GI tract. However, antibiotics can disrupt the normal intestinal flora, leading to an overgrowth of *clostridium difficile*. In certain examples, the *clostridium difficile* spores can be resistant to various antibiotics. Thus, as the normal intestinal flora is cleared, the *clostridium difficile* spores remain, leading to a large population of *clostridium difficile*.

OVERVIEW

This document discusses, among other things, receiving a plurality of donor fecal samples from a plurality of donors and storing and indexing each respective donor fecal samples using at least one characteristic of the respective donor fecal sample. In an example, the donor fecal sample can be screened and processed for subsequent use in fecal bacteriotherapy to displace pathogenic or undesired organisms in the digestive track of a patient with healthy or desirable gut micriobiota.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
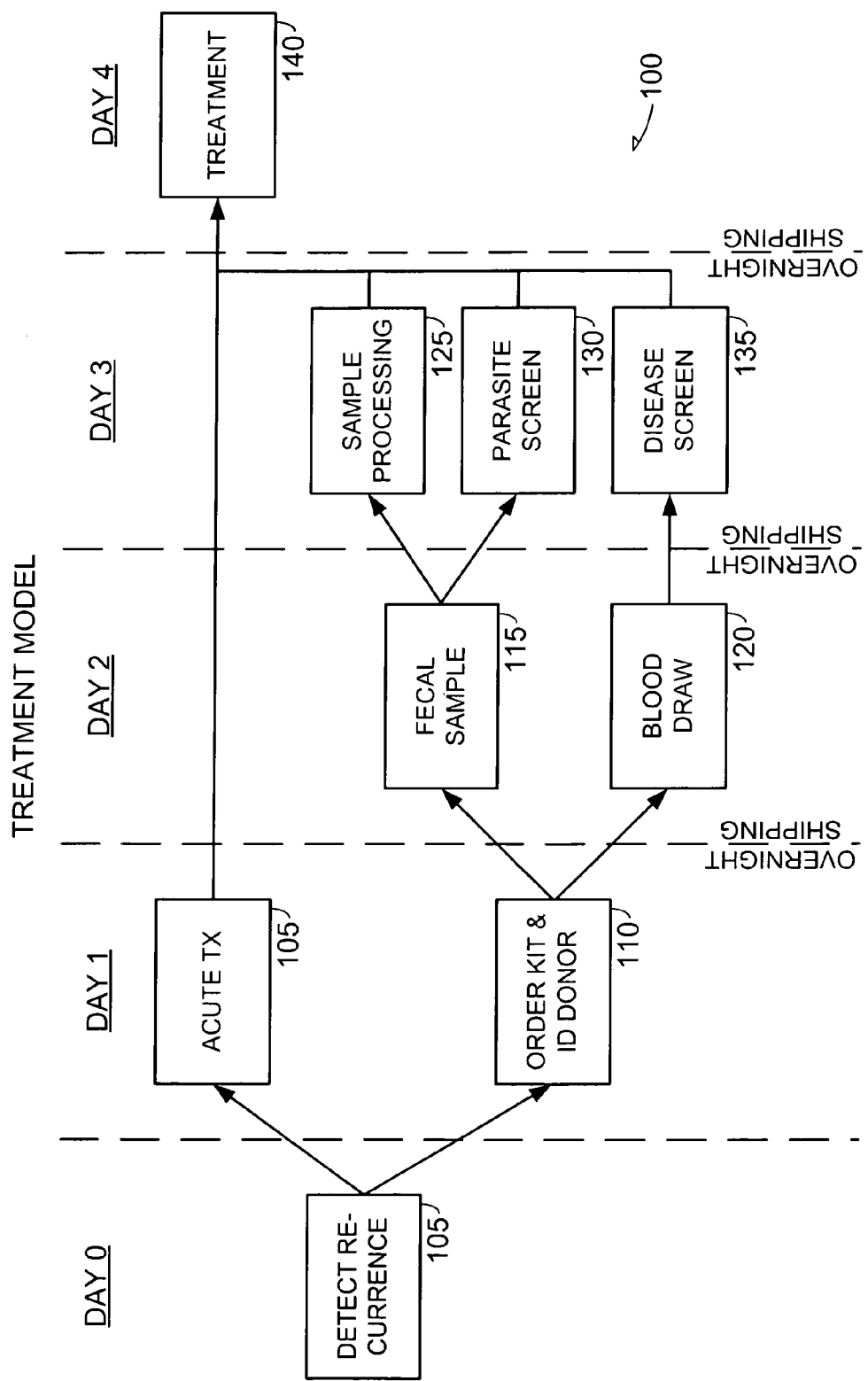
FIG. 1 illustrates generally an example of a Treatment Model including a 5 day fecal bacteriotherapy treatment cycle.

Each individual has a personalized gut microbiota including an estimated 500 to 5000 or more species of bacteria, fungi, archaea and other microorganisms, up to 100 trillion individual organisms, that reside in the digestive tract, providing a host of useful symbiotic functions, including aiding in digestion, providing nutrition for the colon, producing vitamins, stimulating the immune system, assisting in defense against exogenous bacteria, modulating energy metabolism, etc. However, an improperly balanced or functioning gut microbiota may play a role in certain diseases or afflictions, such as pseudomembranous colitis, *clostridium difficile* colitis, antibiotic-associated diarrhea (AAD), ulcerative colitis (UC), pouchitis, irritable bowel syndrome (IBS), obesity, among others.

Accordingly, the present inventor has recognized, among other things, systems and methods for providing bacteriotherapy to treat afflictions associated with the gut microbiota, including *clostridium difficile* colitis, by displacing pathogenic organisms in the digestive track of a patient with healthy bacterial flora, or bacterial flora intended to benefit a specific individual with an affliction associated with the gut microbiota. In an example, the systems and methods described herein can provide a convenient, hygienic mechanism, capable of meshing with existing capabilities and routines of existing clinics and hospitals, for providing bacteriotherapy to a patient. In certain examples, similar treatment can be effective for patients with other diseases, such as IBS, crones, ulcer, or other gastrointestinal or digestive tract related disease. In other examples, bacteriotherapy can be used to aid in weight loss, displacing ineffective flora in the gut with a more effective microbiota.

For example, estimates of *clostridium difficile* overpopulation incidence vary from 1.5 to 2.7 million occurrences in the United States per year, and are growing. In one estimate, hospital discharges with *clostridium difficile* doubled from 2001 to 2005, with an estimated 5% to 25% compound annual growth rate. Current estimates indicate that patients affected by *clostridium difficile* overpopulation experience increased hospital stays from 3 to 36 days, with nearly 20% of affected patients being readmitted within 180 days, each more likely to be discharged to long-term care facilities than patients not affected. The financial impact of *clostridium difficile* is estimated at $1 to $3 billion annually. Moreover, an estimated 300 patient deaths per day are attributable to *clostridium difficile* overpopulation, a mortality rate of 1 to 7.7%, and increasing.

Traditional treatment for *clostridium difficile* typically includes application antibiotics. Metronidazole ("Flagyl®") is the antibiotic of choice due to low price and high efficacy. However, for recurring cases (up to 20% of total cases, for example, resistant to metronidazole), pregnant patients, or patients younger than 10 years of age, vancomycin ("Vancocin®") is typically used. However, vancomycin, although typically having fewer side effects than metronidazole, has a much higher cost and may lead to resistance of existing *clostridium difficile* to further antibiotics.

At first occurrence, antibiotic treatment for *clostridium difficile* can be acutely effective to treat diarrhea within 2 to 4 days at a rate approximately at or above 90%. However, *clostridium difficile* typically recurs after the first occurrence (e.g., several days to 12 weeks after cessation of antibiotics) at an estimated 20% rate (e.g., 15%-30%). However, for each recurrence following the first recurrence, the rate increases greatly, to an estimated 40% rate following the second recurrence, and to greater than an estimated 60% rate or greater thereafter. It is estimated that approximately 5% of patients have 6 or more recurrences.

Treatment for *clostridium difficile* typically varies after each occurrence. For example, for first mild to moderate recurrence, metronidazole can be administered orally (e.g., at a dose of 500 mg, three times daily ("TID") for 10 to 14 days). For a second recurrence, vancomycin can be administered orally in tapered or pulsed doses (e.g., at a dose of 125 mg, four times daily ("QID") for 14 days; at a dose of 125 mg, twice daily ("BID") for 7 days; at a dose of 125 mg, once daily ("QD") for 7 days; at a dose of 125 mg, once every 2 days for 8 days (four doses); at a dose of 125 mg, once every 3 days for 15 days (five doses), etc.). For a third recurrence, vancomycin can be applied at greater doses (e.g., at a dose of 125 mg, four times daily ("QID") for 14 days), combined with any of the other options for recurrent infection, such as intravenous immunoglobulin (e.g., at a dose of 400 mg per kg body weight, once every three weeks, for a total of two or three doses depending on effect), or rifamycin following the vancomycin doses (e.g., the rifamycin at a dose of 400 mg, twice daily ("BID") for 14 days), etc.

In an example, bacteriotherapy to treat *clostridium difficile* or one or more other diseases or afflictions of the digestive tract can be provided using a combination of antibiotics and re-population of a healthy or desired bacterial flora. In certain examples, the re-population of bacterial flora can include fecal bacteriotherapy, or fecal transplant.

The process of fecal bacteriotherapy can include introducing a fecal sample of a healthy donor, or a donor having one or more desired characteristics, into a gastrointestinal tract of a patient to repopulate a healthy or desirable gut microbiota. In certain examples, prior to introduction of the fecal sample, the patient's intestinal flora can be disrupted using antibiotics, such that the healthy or desirable gut microbiota, once introduced into the patient, can easily populate the gastrointestinal tract.

In an example, a kit of parts can be created to aid in fecal transplant. In an example, a donation kit can be shipped to a clinician. The donation kit can include equipment for blood and fecal samples from the patient or, in certain examples, a healthy donor. Because much of the patient's gut micriobiota is anaerobic, many organisms can die with exposure to air. In an example, the donation kit can include materials to ship the blood and fecal samples without harming the samples (e.g., quick freeze, dry ice, etc.).

Once shipped to a facility (e.g., one location, regional locations, many locations, etc.), the samples can be tested, and *clostridium difficile* or the presence or absence of one or more other diseases or conditions can be confirmed. In other examples, a healthy fecal sample can be tested and prepared for use as a treatment.

In an example, once the patient's samples are tested to verify the disease or condition, or the donor's samples are tested to verify health or other compatibility (e.g., the existence of one or more desired condition, etc.), a treatment can be prepared (e.g., using the healthy donor fecal sample, at least a portion of one or more healthy stored fecal samples, such as material from a fecal bank, etc.) and shipped back to the clinician for delivery to and treatment of the patient. In certain examples, the treatment is preserved (e.g., frozen, etc.) during shipping. The kit can include the processed fecal sample or treatment in a sterile container, such as a nasogastric (NG) tube, a vial (e.g., for use with a retention enema), a gastro-resistant capsule (e.g., acid-bio resistant to reach the intestinal tract, having a sterile outside), etc. In an example, once received, the clinician can store the contents in a manner to preserve the micriobiota until ready to be inserted into the patient.

FIG. 1 illustrates generally an example of a Treatment Model 100 including a 5 day fecal bacteriotherapy treatment cycle. At 105, day 0, recurrence of a condition, such as *clostridium difficile* colitis or one or more other afflictions associated with the gut microbiota, is detected in a patient. In an example, the condition can be detected using the presentation of one or more symptoms associated with the condition, such as diarrhea during or following hospitalization, etc. In other examples, at 105, the occurrence of one or more undesirable conditions, such as obesity, etc., can be detected, triggering application of the Treatment Model 100.

At 105, day 1, acute treatment ("TX") can be prescribed for or administered to the patient. In an example, the acute treatment can include administration of vancomycin (e.g., at a dose of 125 mg) four times daily for 4 days (QID×4d). In other examples, other doses can be used. However, the dosage can be less than traditional antibiotic treatment due to the subsequent repopulation of healthy or desired gut micriobiota from the fecal bacteriotherapy to combat conditions or pathogens that would otherwise remain in the gastrointestinal tract (e.g., *clostridium difficile* spores, etc.).

At 110, day 1, a bacteriotherapy kit can be ordered, and in certain examples, a donor can be identified. In an example, the bacteriotherapy kit can be directed for use with a specific donor and recipient. In many examples, for patients or intended recipients having an improperly balanced or functioning gut microbiota, it can be desirable to identify a donor having a healthy gut microbiota similar to the patient's healthy gut microbiota. Accordingly, a donor having a similar diet from a similar or close geographic region, typically a spouse or close relative, provides the best probability of quickly returning the patient's healthy gut microbiota. However, in other examples, other desired donor characteristics can be selected, such as a physical characteristic, etc. In an example, the bacteriotherapy kit can be overnight shipped to a clinician at a treatment facility, such as a hospital or clinic, or otherwise quickly delivered to or stocked by the clinician or at the treatment facility. In certain examples, the kit can include a cooling mechanism, such as dry ice or one or more other cooling mechanisms, configured to preserve subsequent biological samples during transport.

At 115, day 2, the fecal sample can be taken from a proposed donor, from the patient, or from both the proposed donor and the patient. At 120, day 2, a blood sample can be taken from the proposed donor, from the patient, or from both the proposed donor and the patient. In an example, the fecal sample and the blood draw can be stored in a bag (e.g., a fecal sample bag or a blood bag, respectively) or one or more other storage mediums, such as a test tube or one or more other storage containers. In certain examples, to preserve the samples for testing and subsequent use, at least one of the fecal sample or the blood draw can be cooled, such as by using dry ice, etc. In an example, the fecal sample and the blood draw can be overnight shipped or otherwise quickly delivered to a facility for testing and processing the donor fecal sample.

At 125, day 3, the fecal sample can be processed for use in fecal bacteriotherapy. In an example, the processing can include at least one of blending or filtering the fecal sample and preparing the sample for delivery to the patient, such as by nasogastric (NG) tube, retention enema, colonoscopy delivery, or an oral tablet or capsule, resistant to stomach acid (e.g., using an enteric coating, etc.), configured to reach the gastrointestinal tract. Accordingly, the processing can include placement into a sterile delivery container, such as a bag configured for use with an NG tube or retention enema. At 130, day 3, the fecal sample can be screened for parasites or other pathogens, prior to or after processing. At 135, day 3, the blood draw can be screened for communicable disease, to further ensure a healthy donor fecal sample.

In an example, following screening and processing, the processed sample can be cooled and overnight shipped to the clinician or caregiver at the treatment facility. At 140, day 4, following the last dose of acute treatment (e.g., using antibiotics), fecal bacteriotherapy can be provided to the patient using the donor's processed fecal sample.

Figure 2:
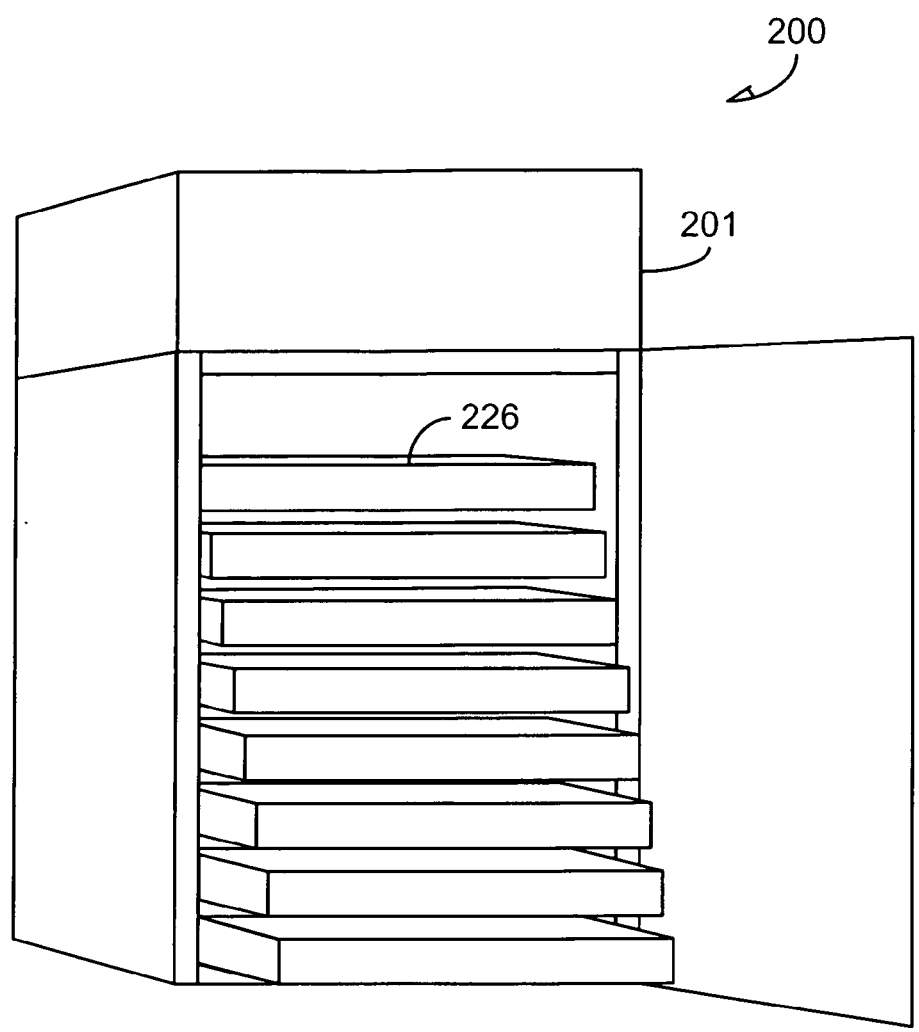
FIG. 2 illustrates generally an example of a bacteriotherapy bank configured to store one or more processed and screened donor fecal samples.

FIG. 2 illustrates generally an example of a bacteriotherapy bank 200 including a cooling device (e.g., a refrigerator 201, etc.) having a plurality of shelves (e.g., such as a first shelf 226, etc.) configured to store one or more processed and screened donor fecal samples. In an example, the bacteriotherapy bank 200 can be configured to provide healthy donor fecal samples to a single patient or a plurality of patients using at least a portion of a fecal sample from a single healthy donor, or using at least a portion of a fecal sample from a plurality of healthy donors. The fecal bank allows for treatment of a first number of patients with a smaller number of donors, reducing the cost of testing and screening the donors and testing, screening, and processing the donor fecal samples.

In an example, the bacteriotherapy bank 200 can be supplied using a pool of anonymous, pre-screened donors, and can stock a number of frozen, screened aliquots (single donor) for subsequent use. In an example, a healthy donor can prepare fecal and blood samples, unattached to a specific patient. In an example, the donor fecal samples can be indexed using various donor information, or using one or more characteristic of the donor fecal sample, such as a geographic location of the donor, the source of the donor's diet, the type of the donor's diet, the donor's ethnicity, body type, age, sex, health status, or medical history, or other information of the donor or the donor's fecal sample. In an example, people in the same geographic location, or having similar diets, can have similar gut microbiota. It can be desirable to match the gut micriobiota of the healthy donor to the patient (e.g., similar reasons to using a healthy family member for a donor). In an example, the donor samples can be indexed using a computer indexing system configured to store the various donor information or one or more characteristic, can be indexed using a label on a bag or shelf in the bacteriotherapy bank 200, or can be indexed using one or more other indexing operations.

In an example, using the bacteriotherapy bank 200, exposure and risk associated with the procedure can be limited by using a donor for only a specified number of samples (e.g., to prevent the accidental exposure of patients to infected donor material). In other examples, it can be advantageous for an obese patient to receive the gut microbiota of a healthy or thin donor, or of a donor having a desired body composition or type, as the healthy or thin donors gut flora may aid in weight management or management of one or more other characteristic, such as weight gain, etc.

In certain examples, the bacteriotherapy bank 200 can store material at temperatures of −20 degrees Celsius, the materials including donor fecal samples, processed fecal samples, fecal samples in delivery form, such as in an NG tube, vial, oral pill, etc., or one or more other material.

Figure 3:
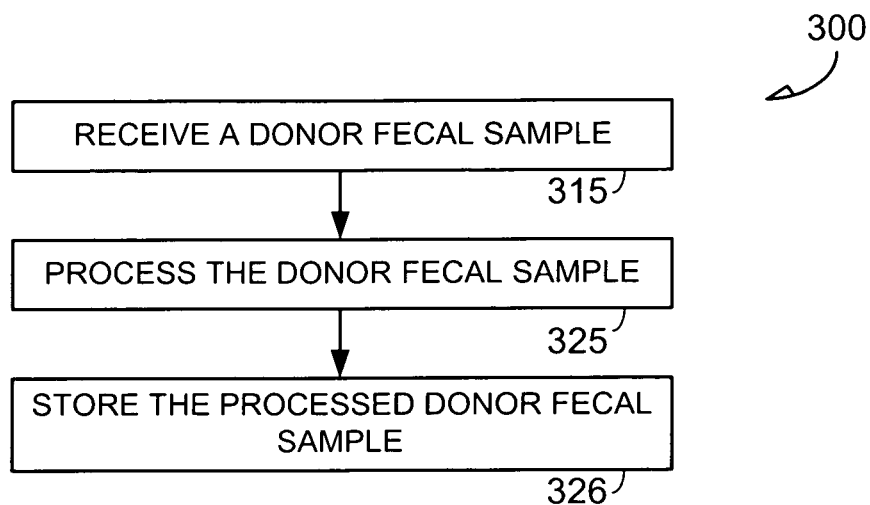
FIG. 3 illustrates generally an example of a method of receiving and storing donor fecal samples.

FIG. 3 illustrates generally an example of a method 300 of receiving and storing donor fecal samples. At 315, a donor fecal sample is received. At 325, the donor fecal sample can be processed and prepared for use in fecal bacteriotherapy, including, in certain examples, testing or screening the donor fecal sample for one or more diseases or conditions, or placing the processed donor fecal sample in deliverable form. At 326, the processed donor fecal sample can be stored prior to use, such as using a cooling mechanism such as dry ice, a refrigerator, or one or more other mechanisms.

Figure 4:
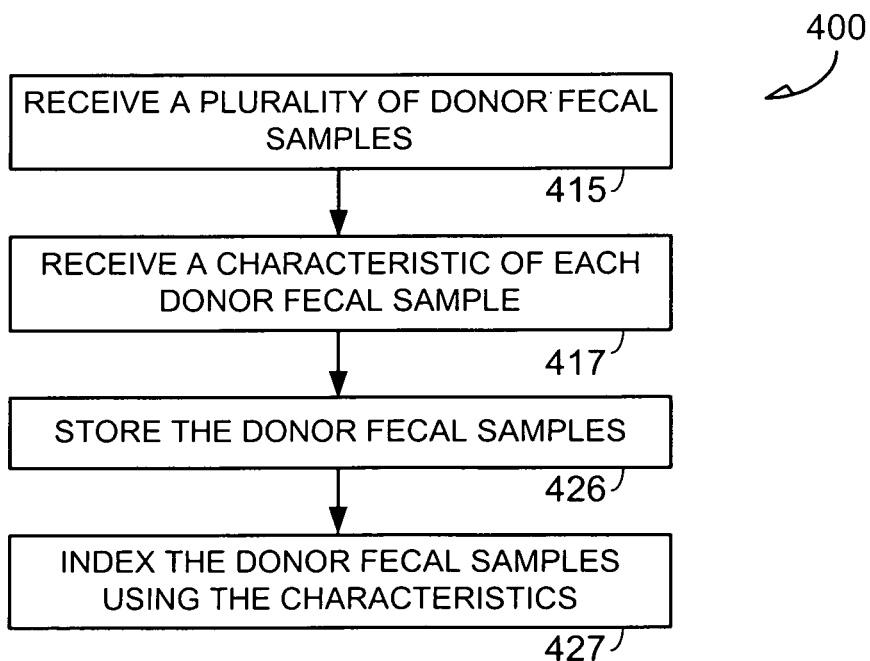
FIG. 4 illustrates generally an example of a method of receiving, storing, and indexing donor fecal samples.

FIG. 4 illustrates generally an example of a method 400 of receiving, storing, and indexing donor fecal samples. At 415, a plurality of donor fecal samples are received. At 417, at least one characteristic of each donor fecal sample, or at least one characteristic of each donor of each donor fecal sample, is received. At 426, the donor fecal sample can be stored prior to use, such as using a cooling mechanism such as dry ice, a refrigerator, or one or more other mechanisms. At 427, the donor fecal samples can be indexed using the at least one characteristic. In certain examples, the donor fecal samples can be selected for use with a patient using one or more shared or desired characteristic.

In other examples, fecal bacteriotherapy (e.g., using the bacteriotherapy bank or kit models described above) can be used to treat or affect one or more other diseases or conditions. For example, inflammatory bowel disease (IBD) (e.g., including Crohn's disease, ulcerative colitis (UC), pouchitis, etc.) affects more than one million people in the United States alone. Irritable bowel syndrome accounts for nearly one-third of all gastrointestinal office visits, affecting more than 36 million patients, with few tools or treatments available to provide effective treatment. In certain examples, patients afflicted with IBD or IBS could benefit from a different gut microbiota providing different functions to the gastrointestinal tract.

Further, fecal bacteriotherapy can be used to treat obesity. Because the gut micriobiota in obese individuals is different from non-obese individuals, and because gut micriobiota influences energy metabolism, displacing the gut micriobiota of an obese individual with the guy micriobiota of a non-obese individual.

Additional Notes & Examples

In Example 1, a method can optionally include receiving a plurality of donor fecal samples from a plurality of donors, receiving a characteristic of each of the plurality of donor fecal samples, storing at least a portion of each of the plurality of donor fecal samples, and indexing each of the plurality of donor fecal samples using a characteristic of the respective donor fecal sample.

In Example 2, a characteristic of the donor fecal sample of Example 1 can optionally include a characteristic of the fecal biota of the donor fecal sample.

In Example 3, the characteristic of the donor fecal sample of any one or more of Examples 1-2 can optionally include at least one of a physical characteristic or a dietary characteristic of the donor.

In Example 4, the physical characteristic of the donor of any one or more of Examples 1-3 can optionally include at least one of a medical condition of the donor, a donor body mass index (BMI), a donor weight, a combination of a donor height and the donor weight, or a donor body fat percentage.

In Example 5, the physical characteristic of the donor of any one or more of Examples 1-4 can optionally include a medical condition of the donor, and the characteristic of the donor fecal sample can optionally include the presence or absence of a medical condition of the donor.

In Example 6, the medical condition of the donor of any one or more of Examples 1-5 can optionally include at least one of a metabolic disorder or a digestive disorder.

In Example 7, the metabolic disorder of any one or more of Examples 1-6 can optionally include diabetes mellitus, and the digestive disorder of any one or more of Examples 1-6 can optionally include a gastrointestinal (GI) disorder including at least one of irritable bowel syndrome (IBS) or inflammatory bowel disease (IBD).

In Example 8, the dietary characteristic of the donor of any one or more of Examples 1-7 can optionally include at least one of a donor geographic consumption region, a donor diet, or a donor religion.

In Example 9, the receiving the plurality of donor fecal samples of any one or more of Examples 1-8 can optionally include processing each of the plurality of donor fecal samples, including homogenizing and filtering each of the donor fecal samples.

In Example 10, the receiving the plurality of donor fecal samples of any one or more of Examples 1-9 can optionally include receiving a plurality of donor fecal samples from a plurality of screened donors.

In Example 11, any one or more of Examples 1-10 can optionally include receiving a request for donor fecal matter, and selecting a fecal dose using information from the request and the indexed characteristics of the plurality of donor fecal samples, wherein the fecal dose optionally includes at least a portion of at least one of the stored donor fecal samples and is configured to be provided to a patient.

In Example 12, any one or more of Examples 1-11 can optionally include providing the fecal dose to the patient to transfer a functioning biota in the patient.

In Example 13, the providing the fecal dose to the patient to transfer the functioning biota in the patient of any one or more of Examples 1-12 can optionally include to treat at least one of antibiotic associated diarrhea or a *Clostridium difficile* infection.

In Example 14, the receiving the request for donor fecal matter of any one or more of Examples 1-13 can optionally include receiving at least one desired characteristic.

In Example 15, the receiving the at least one desired characteristic of any one or more of Examples 1-14 can optionally include receiving at least one of a desired physical characteristic or a desired dietary characteristic of the donor.

In Example 16, the storing at least a portion of each of the plurality of donor fecal samples of any one or more of Examples 1-15 can optionally include storing at least a portion of each of the plurality of donor fecal samples in a patient-deliverable form.

In Example 17, the storing at least a portion of each of the plurality of donor fecal samples in the patient-deliverable form of any one or more of Examples 1-16 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 18, the receiving the plurality of donor fecal samples of any one or more of Examples 1-17 can optionally include receiving wet fecal samples and processing each of the received donor fecal samples, wherein the processing each of the received donor fecal samples of any one or more of Examples 1-17 can optionally include homogenizing, filtering, and adding a cryoprotectant to each of the donor fecal samples, and wherein the storing at least a portion of each of the plurality of donor fecal samples in a patient-deliverable form of any one or more of Examples 1-17 can optionally include freezing each of the plurality of donor fecal samples in the patient-deliverable form to maintain viability of the biota of the donor fecal samples.

In Example 19, any one or more of Examples 1-18 can optionally include preparing a plurality of fecal doses using one or more donor fecal samples from a single donor, wherein the plurality of fecal doses are configured to be provided to a plurality of patients.

In Example 20, any one or more of Examples 1-19 can optionally include preparing a fecal dose configured to be provided to a single patient using a plurality of donor fecal samples.

In Example 21, the preparing the fecal dose of any one or more of Examples 1-20 can optionally include combining at least a portion of a first donor fecal sample and a second donor fecal sample, wherein the first and second donor samples have at least one different characteristic.

In Example 22, a fecal bank can optionally include a plurality of fecal storage containers configured to store each of a plurality of donor fecal sample and an indexing system, configured to associate, for each of the plurality of donor fecal samples, a characteristic of the donor fecal sample with the respective donor fecal sample.

In Example 23, the characteristic of the donor fecal sample of any one or more of Examples 1-22 can optionally include at least one of a physical characteristic or a dietary characteristic of the donor.

In Example 24, the characteristic of the donor fecal sample of any one or more of Examples 1-23 can optionally include a characteristic of the fecal biota of the donor fecal sample.

In Example 25, the physical characteristic of the donor of any one or more of Examples 1-24 can optionally include at least one of a medical condition of the donor, a donor body mass index (BMI), a donor weight, a combination of a donor height and the donor weight, or a donor body fat percentage.

In Example 26, the physical characteristic of the donor of any one or more of Examples 1-25 can optionally include a medical condition of the donor and wherein the characteristic of the donor fecal sample includes the presence or absence of a medical condition of the donor.

In Example 27, the medical condition of the donor of any one or more of Examples 1-26 can optionally include at least one of a metabolic disorder or a digestive disorder, wherein the metabolic disorder includes diabetes mellitus, and wherein the digestive disorder includes a gastrointestinal (GI) disorder including at least one of irritable bowel syndrome (IBS) or inflammatory bowel disease (IBD).

In Example 28, the dietary characteristic of the donor of any one or more of Examples 1-27 can optionally include at least one of a donor geographic consumption region, a donor diet, or a donor religion.

In Example 29, the plurality of donor fecal samples of any one or more of Examples 1-28 can optionally include wet fecal samples and wherein the plurality of fecal storage containers are configured to store frozen, wet donor fecal samples to maintain viability of the biota of the donor fecal samples.

In Example 30, the plurality of fecal storage containers of any one or more of Examples 1-29 can optionally include a plurality of patient-deliverable fecal storage containers.

In Example 31, the plurality of patient-deliverable fecal storage containers of any one or more of Examples 1-30 can optionally include at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retraograde GI delivery approach to the intestinal tract of the patient.

In Example 32, a system can include, or can optionally be combined with any portion or combination of any portions of any one or more of Examples 1-31 to include, subject matter that can include means for performing any one or more of the functions of Examples 1-31, or a machine-readable medium including instructions that, when performed by a machine, cause the machine to perform any one or more of the functions of Examples 1-31.

In Example 33, a method optionally includes receiving a donor fecal sample from a donor, processing the donor fecal sample, wherein the processing includes homogenizing the donor fecal sample, and storing at least a portion of the processed donor fecal sample.

In Example 34, the receiving the donor fecal sample from the donor of any one or more of Examples 1-33 can optionally include receiving a plurality of donor fecal samples from a plurality of donors, wherein the processing the donor fecal sample of any one or more of Examples 1-33 can optionally include processing each of the plurality of donor fecal samples, wherein the processing of any one or more of Examples 1-33 can optionally include homogenizing each of the donor fecal samples, and wherein the storing at least a portion of the processed donor fecal sample of any one or more of Examples 1-33 can optionally include storing at least a portion of each of the plurality of processed donor fecal samples.

In Example 35, any one or more of Examples 1-34 optionally includes receiving a characteristic of each of the plurality of donor fecal samples, and indexing each of the plurality of donor fecal samples using a characteristic of the respective donor fecal sample.

In Example 36, the characteristic of the donor fecal sample of any one or more of Examples 1-35 can optionally include a characteristic of the fecal biota of the donor fecal sample.

In Example 37, the characteristic of the donor fecal sample of any one or more of Examples 1-36 can optionally include at least one of a physical characteristic or a dietary characteristic of the donor.

In Example 38, the physical characteristic of the donor of any one or more of Examples 1-37 can optionally include at least one of a medical condition of the donor, a donor body mass index (BMI), a donor weight, a combination of a donor height and the donor weight, or a donor body fat percentage.

In Example 39, the physical characteristic of the donor of any one or more of Examples 1-38 can optionally include a medical condition of the donor, and wherein the characteristic of the donor fecal sample of any one or more of Examples 1-38 can optionally include the presence or absence of a medical condition of the donor.

In Example 40, the medical condition of the donor of any one or more of Examples 1-39 can optionally include at least one of a metabolic disorder or a digestive disorder, wherein the metabolic disorder of any one or more of Examples 1-39 can optionally include diabetes mellitus, and wherein the digestive disorder includes a gastrointestinal (GI) disorder of any one or more of Examples 1-39 can optionally include at least one of irritable bowel syndrome (IBS) or inflammatory bowel disease (IBD).

In Example 41, the dietary characteristic of the donor of any one or more of Examples 1-40 can optionally include at least one of a donor geographic consumption region, a donor diet, or a donor religion.

In Example 42, any one or more of Examples 1-41 can optionally, include receiving a request for donor fecal matter, and selecting a fecal dose using information from the request and the indexed characteristics of the plurality of donor fecal samples, wherein the fecal dose of any one or more of Examples 1-41 can optionally include at least a portion of at least one of the stored donor fecal samples and is configured to be provided to a patient.

In Example 43, any one or more of Examples 1-42 can optionally include providing the fecal dose to the patient to transfer a functioning biota in the patient.

In Example 44, the providing the fecal dose to the patient to transfer the functioning biota in the patient of any one or more of Examples 1-43 can optionally include to treat at least one of antibiotic associated diarrhea or a *Clostridium difficile* infection.

In Example 45, the receiving the request for donor fecal matter of any one or more of Examples 1-44 can optionally include receiving at least one desired characteristic.

In Example 46, the receiving the at least one desired characteristic of any one or more of Examples 1-45 can optionally include receiving at least one of a desired physical characteristic or a desired dietary characteristic of the donor.

In Example 47, any one or more of Examples 1-46 can optionally include preparing a fecal dose configured to be provided to a single patient using a plurality of processed donor fecal samples.

In Example 48, the preparing the fecal dose of any one or more of Examples 1-47 can optionally include combining at least a portion of a first donor fecal sample and a second donor fecal sample, wherein the first and second donor samples have at least one different characteristic.

In Example 49, the processing the donor fecal sample of any one or more of Examples 1-48 can optionally include filtering the donor fecal sample.

In Example 50, the receiving the donor fecal sample of any one or more of Examples 1-49 can optionally include receiving a donor fecal sample from a screened donor.

In Example 51, the storing at least a portion of the processed donor fecal sample of any one or more of Examples 1-50 can optionally include storing at least a portion of the processed donor fecal sample in a patient-deliverable form.

In Example 52, the storing at least a portion of the processed donor fecal sample in the patient-deliverable form of any one or more of Examples 1-51 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retraograde GI delivery approach to the intestinal tract of the patient.

In Example 53, the receiving the donor fecal sample of any one or more of Examples 1-52 can optionally include receiving a wet fecal sample, wherein the processing the donor fecal sample of any one or more of Examples 1-52 can optionally include adding a cryoprotectant to the donor fecal sample, and wherein the storing at least a portion of the processed donor fecal sample in the patient-deliverable form of any one or more of Examples 1-52 can optionally include freezing at least a portion of the processed donor fecal sample in the patient-deliverable form to maintain viability of the biota of the donor fecal sample.

In Example 54, the adding the cryoprotectant of any one or more of Examples 1-53 can optionally include at least one of glycol, glycerol, dimethyl sulfoxide (DMSO), dairy milk, or soy milk.

In Example 55, any one or more of Examples 1-54 can optionally include preparing a plurality of fecal doses using one or more processed donor fecal samples from a single donor, wherein the plurality of fecal doses are configured to be provided to a plurality of patients.

In Example 56, at least a portion of the stored donor fecal sample of any one or more of Examples 1-55 can optionally be configured to be provided to an intestinal tract of a patient that is not the donor to a condition of the patient.

In Example 57, the condition of any one or more of Examples 1-56 can optionally include at least one of a disease or an infection of or in the patient.

In Example 58, the condition of any one or more of Examples 1-57 can optionally include at least one of antibiotic associated diarrhea of the patient or a *Clostridium difficile* infection in the patient.

In Example 59, a system can include, or can optionally be combined with any portion or combination of any portions of any one or more of Examples 1-58 to include, subject matter that can include means for performing any one or more of the functions of Examples 1-58, or a machine-readable medium including instructions that, when performed by a machine, cause the machine to perform any one or more of the functions of Examples 1-58.

In Example 60, a method can optionally include receiving a donor fecal sample from a donor, and storing at least a portion of the donor fecal sample in a patient-deliverable form.

In Example 61, the receiving the donor fecal sample of any one or more of Examples 1-60 can optionally include receiving a plurality of donor fecal samples from a plurality of donors, and wherein the storing at least a portion of the donor fecal sample in the patient-deliverable from of any one or more of Examples 1-60 can optionally include storing at least a portion of each of the plurality of processed donor fecal samples in a patient-deliverable form.

In Example 62, any one or more of Examples 1-61 can optionally include receiving a characteristic of each of the plurality of donor fecal samples, and indexing each of the plurality of donor fecal samples using a characteristic of the respective donor fecal sample.

In Example 63, the characteristic of the donor fecal sample of any one or more of Examples 1-62 can optionally include a characteristic of the fecal biota of the donor fecal sample.

In Example 64, the characteristic of the donor fecal sample of any one or more of Examples 1-63 can optionally include at least one of a physical characteristic or a dietary characteristic of the donor.

In Example 65, the physical characteristic of the donor of any one or more of Examples 1-64 can optionally include at least one of a medical condition of the donor, a donor body mass index (BMI), a donor weight, a combination of a donor height and the donor weight, or a donor body fat percentage.

In Example 66, the physical characteristic of the donor of any one or more of Examples 1-65 can optionally include a medical condition of the donor and wherein the characteristic of the donor fecal sample of any one or more of Examples 1-65 can optionally include the presence or absence of a medical condition of the donor.

In Example 67, the medical condition of the donor of any one or more of Examples 1-66 can optionally include at least one of a metabolic disorder or a digestive disorder, wherein the metabolic disorder of any one or more of Examples 1-66 can optionally include diabetes mellitus, and wherein the digestive disorder of any one or more of Examples 1-66 can optionally include a gastrointestinal (GI) disorder including at least one of irritable bowel syndrome (IBS) or inflammatory bowel disease (IBD).

In Example 68, the dietary characteristic of the donor of any one or more of Examples 1-67 can optionally include at least one of a donor geographic consumption region, a donor diet, or a donor religion.

In Example 69, any one or more of Examples 1-68 can optionally include receiving a request for donor fecal matter and selecting a fecal dose using information from the request and the indexed characteristics of the plurality of donor fecal samples, wherein the fecal dose includes at least a portion of at least one of the stored donor fecal samples and is configured to be provided to a patient.

In Example 70, any one or more of Examples 1-69 can optionally include providing the fecal dose to the patient to transfer a functioning biota in the patient.

In Example 71, the providing the fecal dose to the patient to transfer the functioning biota in the patient of any one or more of Examples 1-70 can optionally include to treat at least one of antibiotic associated diarrhea or a *Clostridium difficile* infection.

In Example 72, the receiving the request for donor fecal matter of any one or more of Examples 1-71 can optionally include receiving at least one desired characteristic.

In Example 73, the receiving the at least one desired characteristic of any one or more of Examples 1-72 can optionally include receiving at least one of a desired physical characteristic or a desired dietary characteristic of the donor.

In Example 74, any one or more of Examples 1-73 can optionally include preparing a fecal dose configured to be provided to a single patient using a plurality of processed donor fecal samples.

In Example 75, the preparing the fecal dose of any one or more of Examples 1-74 can optionally include combining at least a portion of a first donor fecal sample and a second donor fecal sample, wherein the first and second donor samples have at least one different characteristic.

In Example 76, the receiving the donor fecal sample of any one or more of Examples 1-75 can optionally include receiving a donor fecal sample from a screened donor.

In Example 77, any one or more of Examples 1-76 can optionally include processing the received donor fecal sample, wherein the processing includes homogenizing the donor fecal sample, wherein the storing at least a portion of the donor fecal sample in the patient-deliverable form of any one or more of Examples 1-76 can optionally include storing at least a portion of the processed donor fecal sample.

In Example 78, the processing the donor fecal sample of any one or more of Examples 1-77 can optionally include filtering the donor fecal sample.

In Example 79, the receiving the donor fecal sample of any one or more of Examples 1-78 can optionally include receiving a wet fecal sample, wherein the processing the donor fecal sample of any one or more of Examples 1-78 can optionally include adding a cryoprotectant to the donor fecal sample, and wherein the storing at least a portion of the processed donor fecal sample in the patient-deliverable form of any one or more of Examples 1-78 can optionally include freezing at least a portion of the processed donor fecal sample in the patient-deliverable form to maintain viability of the biota of the donor fecal sample.

In Example 80, any one or more of Examples 1-79 can optionally include preparing a plurality of fecal doses using one or more processed donor fecal samples from a single donor, wherein the plurality of fecal doses are configured to be provided to a plurality of patients.

In Example 81, the storing at least a portion of the donor fecal sample in the patient-deliverable form of any one or more of Examples 1-80 can optionally include storing at least a portion of the donor fecal sample in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 82, the storing at least a portion of the donor fecal sample in the ingestible capsule of any one or more of Examples 1-81 can optionally include storing at least a portion of the donor fecal sample in a gastro-resistant capsule.

In Example 83, any one or more of Examples 1-82 can optionally include a patient-deliverable fecal storage container configured to store at least a portion of a processed donor fecal sample configured to be provided to an intestinal tract of a patient that is not the donor to treat a condition of the patient.

In Example 84, of any one or more of Examples 1-83 can optionally include a plurality of patient-deliverable fecal storage containers configured to store at least a portion of each of a plurality of processed donor fecal samples, and an indexing system, configured to associate, for each of the plurality of processed donor fecal samples, a characteristic of the processed donor fecal sample with the respective processed donor fecal sample.

In Example 85, the characteristic of the donor fecal sample of any one or more of Examples 1-84 can optionally include a characteristic of the fecal biota of the donor fecal sample.

In Example 86, the characteristic of the donor fecal sample of any one or more of Examples 1-85 can optionally include at least one of a physical characteristic or a dietary characteristic of the donor.

In Example 87, the physical characteristic of the donor of any one or more of Examples 1-86 can optionally include at least one of a medical condition of the donor, a donor body mass index (BMI), a donor weight, a combination of a donor height and the donor weight, or a donor body fat percentage.

In Example 88, the physical characteristic of the donor of any one or more of Examples 1-87 can optionally include a medical condition of the donor, wherein the characteristic of the donor fecal sample of any one or more of Examples 1-87 can optionally include the presence or absence of a medical condition of the donor.

In Example 89, the medical condition of the donor of any one or more of Examples 1-88 can optionally include at least one of a metabolic disorder or a digestive disorder, wherein the metabolic disorder of any one or more of Examples 1-88 can optionally include diabetes mellitus, and wherein the digestive disorder of any one or more of Examples 1-88 can optionally include a gastrointestinal (GI) disorder including at least one of irritable bowel syndrome (IBS) or inflammatory bowel disease (IBD).

In Example 90, the dietary characteristic of the donor of any one or more of Examples 1-89 can optionally include at least one of a donor geographic consumption region, a donor diet, or a donor religion.

In Example 91, the processed donor fecal sample of any one or more of Examples 1-90 can optionally include a wet fecal sample, and wherein the patient-deliverable fecal storage container of any one or more of Examples 1-90 can optionally be configured to store at least a portion of a frozen, wet donor fecal sample to maintain viability of the biota of the donor fecal sample.

In Example 92, the patient-deliverable fecal storage container of any one or more of Examples 1-91 can optionally include at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retraograde GI delivery approach to the intestinal tract of the patient.

In Example 93, the condition of the patient of any one or more of Examples 1-92 can optionally include at least one of a disease or an infection of or in the patient.

In Example 94, the condition of the patient of any one or more of Examples 1-93 can optionally include at least one of antibiotic associated diarrhea of the patient or a *Clostridium difficile* infection in the patient.

In Example 95, a system can include, or can optionally be combined with any portion or combination of any portions of any one or more of Examples 1-94 to include, subject matter that can include means for performing any one or more of the functions of Examples 1-94, or a machine-readable medium including instructions that, when performed by a machine, cause the machine to perform any one or more of the functions of Examples 1-94.

In Example 96, a method can optionally include selecting a fecal dose for treatment of a condition of a patient, wherein the fecal dose includes at least a portion of a donor fecal sample from a donor and is configured to be provided to an intestinal tract of the patient, wherein the patient is not the donor, and wherein the selecting the fecal dose includes using a characteristic of the donor.

In Example 97, the condition of the patient of any one or more of Examples 1-96 can optionally include a patient weight above a desired target weight.

In Example 98, the condition of the patient of any one or more of Examples 1-97 can optionally include obesity.

In Example 99, the characteristic of the donor fecal sample of any one or more of Examples 1-98 can optionally include a characteristic of the fecal biota of the donor fecal sample.

In Example 100, the characteristic of the donor of any one or more of Examples 1-99 can optionally include at least one of a physical characteristic or a dietary characteristic of the donor.

In Example 101, the physical characteristic of the donor of any one or more of Examples 1-100 can optionally include at least one of a donor body mass index (BMI), a donor weight, a combination of a donor height and the donor weight, or a donor body fat percentage.

In Example 102, the physical characteristic of the donor of any one or more of Examples 1-101 can optionally include a medical condition of the donor, and wherein the characteristic of the donor fecal sample of any one or more of Examples 1-101 can optionally include the presence or absence of a medical condition of the donor.

In Example 103, the dietary characteristic of the donor of any one or more of Examples 1-102 can optionally include at least one of a donor geographic consumption region, a donor diet, or a donor religion.

In Example 104, any one or more of Examples 1-103 can optionally include providing information about the dietary characteristic of the donor to the patient, wherein the dietary characteristic includes a donor diet.

In Example 105, the characteristic of the donor of any one or more of Examples 1-104 can optionally include the physical characteristic of the donor and the dietary characteristic of the donor.

In Example 106, the fecal dose of any one or more of Examples 1-105 can optionally include at least a portion of a plurality of donor fecal samples from a plurality of donors, and wherein the selecting the fecal dose of any one or more of Examples 1-105 can optionally include using at least one characteristic of the plurality of donors.

In Example 107, any one or more of Examples 1-106 can optionally include receiving the donor fecal sample from the donor, processing the donor fecal sample, wherein the processing of any one or more of Examples 1-106 can optionally include homogenizing the donor fecal sample, and wherein the fecal dose of any one or more of Examples 1-106 can optionally include at least a portion of the processed donor fecal sample.

In Example 108, the receiving the donor fecal sample from the donor of any one or more of Examples 1-107 can optionally include receiving a plurality of donor fecal samples from a plurality of donors, wherein the processing the donor fecal sample of any one or more of Examples 1-107 can optionally include processing each of the plurality of donor fecal samples, wherein the processing of any one or more of Examples 1-107 can optionally include homogenizing each of the donor fecal samples, and storing at least a portion of each of the plurality of processed donor fecal samples.

In Example 109, any one or more of Examples 1-108 can optionally include receiving a characteristic of each of the plurality of donor fecal samples, and indexing each of the plurality of donor fecal samples using a characteristic of the respective donor fecal sample.

In Example 110, the fecal dose of any one or more of Examples 1-109 can optionally include at least a portion of at least one of the stored processed donor fecal samples and is configured to be provided to a patient.

In Example 111, the receiving the donor fecal sample of any one or more of Examples 1-110 can optionally include receiving a wet fecal sample, wherein the processing the donor fecal sample includes adding a cryoprotectant to the donor fecal sample, storing at least a portion of the processed donor fecal sample in a patient-deliverable form, and wherein the storing at least a portion of the processed donor fecal sample in the patient-deliverable form of any one or more of Examples 1-110 can optionally include freezing at least a portion of the processed donor fecal sample in the patient-deliverable form to maintain viability of the biota of the donor fecal sample.

In Example 112, any one or more of Examples 1-111 can optionally include receiving the donor fecal sample from the donor, storing at least a portion of the donor fecal sample in a patient-deliverable form, and wherein the selecting the fecal dose of any one or more of Examples 1-111 can optionally include selecting at least one stored donor fecal sample.

In Example 113, the storing at least a portion of the donor fecal sample in the patient-deliverable form of any one or more of Examples 1-112 can optionally include storing at least a portion of the donor fecal sample in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 114, the condition of any one or more of Examples 1-113 can optionally include at least one of a disease or an infection of or in the patient.

In Example 115, the condition of any one or more of Examples 1-116 can optionally include at least one of antibiotic associated diarrhea of the patient or a *Clostridium difficile* infection in the patient.

In Example 116, any one or more of Examples 1-115 can optionally include preparing a plurality of fecal doses using one or more donor fecal samples from a single donor, wherein the plurality of fecal doses are configured to be provided to a plurality of patients In Example 117, any one or more of Examples 1-116 can optionally include receiving a plurality of donor fecal samples from a plurality of donors, receiving a characteristic of each of the plurality of donors, storing at least a portion of each of the plurality of donor fecal samples, indexing each of the plurality of donor fecal samples using at least one characteristic of the respective donors, receiving a request for donor fecal matter, and selecting a fecal dose for treatment of a condition of a patient in response to the received request for donor fecal matter, wherein the fecal dose of any one or more of Examples 1-116 can optionally include at least a portion of a stored donor fecal sample and is configured to be provided to an intestinal tract of the patient, wherein the patient is not the donor, wherein the condition of the patient of any one or more of Examples 1-116 can optionally include a patient weight above a desired patient weight, and wherein the selecting the fecal dose includes using a physical characteristic of the donor of the fecal dose and a dietary characteristic of the donor of the fecal dose.

In Example 118, the physical characteristic of the donor of any one or more of Examples 1-117 can optionally include at least one of a donor body mass index (BMI), a donor weight, a combination of a donor height and the donor weight, or a donor body fat percentage.

In Example 119, the dietary characteristic of the donor of any one or more of Examples 1-118 can optionally include at least one of a donor geographic consumption region, a donor diet, or a donor religion.

In Example 120, any one or more of Examples 1-119 can optionally include providing information about the dietary characteristic of the donor to the patient, wherein the dietary characteristic includes a donor diet.

In Example 121, the fecal dose of any one or more of Examples 1-120 can optionally include at least a portion of a plurality of donor fecal samples from a plurality of donors, and wherein the selecting the fecal dose of any one or more of Examples 1-120 can optionally include using a physical characteristic of the plurality of donors of the fecal dose and a dietary characteristic of the plurality of donors of the fecal dose.

In Example 122, a system can include, or can optionally be combined with any portion or combination of any portions of any one or more of Examples 1-121 to include, subject matter that can include means for performing any one or more of the functions of Examples 1-121, or a machine-readable medium including instructions that, when performed by a machine, cause the machine to perform any one or more of the functions of Examples 1-121.

In Example 123, a method can optionally include providing a kit to a clinician, the kit enabling the clinician to store and transport a donor fecal sample from a donor to a central facility, receiving the frozen donor fecal sample from the clinician at the central facility, screening the donor fecal sample for at least one of a parasite, a pathogen, a disease, or an unhealthy condition of the donor, and providing a fecal dose to the clinician to be administered to a patient, wherein the fecal dose includes at least a portion of at least one donor fecal sample.

In Example 124, any one or more of Examples 1-123 can optionally include, receiving a characteristic of the donor fecal sample, storing at least a portion the donor fecal sample, and indexing the donor fecal sample using the characteristic of the donor fecal sample.

In Example 125, the characteristic of the donor fecal sample of any one or more of Examples 1-124 can optionally include a characteristic of the fecal biota of the donor fecal sample.

In Example 126, the characteristic of the donor fecal sample of any one or more of Examples 1-125 can optionally include at least one of a physical characteristic or a dietary characteristic of the donor.

In Example 127, the physical characteristic of the donor of any one or more of Examples 1-126 can optionally include at least one of a medical condition of the donor, a donor body mass index (BMI), a donor weight, a combination of a donor height and the donor weight, or a donor body fat percentage.

In Example 128, the physical characteristic of the donor of any one or more of Examples 1-127 can optionally include a medical condition of the donor, and wherein the characteristic of the donor fecal sample of any one or more of Examples 1-127 can optionally include the presence or absence of a medical condition of the donor.

In Example 129, the medical condition of the donor of any one or more of Examples 1-128 can optionally include at least one of a metabolic disorder or a digestive disorder.

In Example 130, the metabolic disorder of any one or more of Examples 1-129 can optionally include diabetes mellitus, and wherein the digestive disorder of any one or more of Examples 1-129 can optionally include a gastrointestinal (GI) disorder including at least one of irritable bowel syndrome (IBS) or inflammatory bowel disease (IBD).

In Example 131, the dietary characteristic of the donor of any one or more of Examples 1-130 can optionally include at least one of a donor geographic consumption region, a donor diet, or a donor religion.

In Example 132, the providing the kit to the clinician of any one or more of Examples 1-131 can optionally include providing a plurality of kits to one or more clinicians, wherein the receiving the frozen donor fecal sample from the clinician of any one or more of Examples 1-131 can optionally include receiving a plurality of frozen donor fecal samples from one or more clinicians, wherein the screening the donor fecal sample of any one or more of Examples 1-131 can optionally include screening a plurality of donor fecal samples, wherein the receiving the characteristic of the donor fecal sample of any one or more of Examples 1-131 can optionally include receiving a characteristic of each of the plurality of donor fecal samples, wherein the storing at least a portion of the donor fecal sample of any one or more of Examples 1-131 can optionally include storing at least a portion of the plurality of donor fecal samples, and wherein the indexing the donor fecal sample of any one or more of Examples 1-131 can optionally include indexing each the plurality of donor fecal samples using a characteristic of the respective donor fecal sample.

In Example 133, any one or more of Examples 1-132 can optionally include receiving a request for donor fecal matter, and selecting the fecal dose to be provided to the patient from a plurality of stored fecal doses using information from the request and the indexed characteristics of the plurality of donor fecal samples.

In Example 134, the receiving the request for donor fecal matter of any one or more of Examples 1-133 can optionally include receiving at least one desired characteristic.

In Example 135, the receiving the at least one desired characteristic of any one or more of Examples 1-136 can optionally include receiving at least one of a desired physical characteristic or a desired dietary characteristic of the donor.

In Example 136, the storing at least a portion the donor fecal sample of any one or more of Examples 1-135 can optionally include storing at least a portion of the donor fecal sample in a patient-deliverable form.

In Example 137, the storing at least a portion of the donor fecal sample in a patient-deliverable form of any one or more of Examples 1-136 can optionally include storing at least a portion of each of the plurality of donor fecal samples in at least one of an ingestible capsule configured to be delivered to an intestinal tract of a patient through the mouth of the patient, an ampule configured for use in an antegrade gastrointestinal (GI) delivery approach to the intestinal tract of the patient, or an ampule configured for use in a retrograde GI delivery approach to the intestinal tract of the patient.

In Example 138, any one or more of Examples 1-137 can optionally include processing the donor fecal sample, the processing the donor fecal sample of any one or more of Examples 1-137 can optionally include homogenizing and filtering the donor fecal sample.

In Example 139, the processing the donor fecal sample of any one or more of Examples 1-138 can optionally include adding a cryoprotectant to the donor fecal sample, and wherein the storing at least a portion of the donor fecal sample of any one or more of Examples 1-138 can optionally include freezing the donor fecal sample to maintain viability of the biota of the donor fecal sample.

In Example 140, any one or more of Examples 1-139 can optionally include providing the fecal dose to the patient to transfer a functioning biota in the patient.

In Example 141, the providing the fecal dose to the patient to transfer the functioning biota in the patient of any one or more of Examples 1-140 can optionally include to treat at least one of antibiotic associated diarrhea or a *Clostridium difficile* infection.

In Example 142, any one or more of Examples 1-141 can optionally include providing a kit to the clinician, the kit enabling the clinician to store and transport a donor blood sample from the donor to the central facility, receiving the frozen donor blood sample from the clinician at the central facility, and screening the donor blood sample for at least one of a parasite, a pathogen, a disease, or an unhealthy condition of the donor.

In Example 143, the providing the kit to the clinician of any one or more of Examples 1-142 can optionally include providing a kit enabling the clinician to store and transport a wet fecal sample from the patient to the central facility.

In Example 144, the providing the kit to the clinician of any one or more of Examples 1-143 can optionally include providing a kit enabling the clinician to store, freeze, and transport the wet fecal sample from the patient to the central facility.

In Example 145, a system can include, or can optionally be combined with any portion or combination of any portions of any one or more of Examples 1-144 to include, subject matter that can include means for performing any one or more of the functions of Examples 1-144, or a machine-readable medium including instructions that, when performed by a machine, cause the machine to perform any one or more of the functions of Examples 1-144.

In Example 146, a method can optionally include providing a kit to a clinician, the kit enabling the clinician to store and transport a patient fecal sample from a patient to a central facility, receiving the frozen patient fecal sample from the clinician at the central facility, and providing a fecal dose to the clinician to be administered to the patient, wherein the fecal dose of any one or more of Examples 1-145 can optionally include at least a portion of at least one donor fecal sample.

In Example 147, any one or more of Examples 1-146 can optionally include receiving a characteristic of the patient fecal sample, and selecting at least one of a plurality of stored donor fecal samples to be provided to the patient using the received characteristic.

In Example 148, any one or more of Examples 1-147 can optionally include receiving a desired characteristic, and selecting at least one of a plurality of stored donor fecal samples to be provided to the patient using the desired characteristic.

In Example 149, the providing the fecal dose to the clinician of any one or more of Examples 1-148 can optionally include providing the fecal dose in a patient-deliverable form, including at least one of an ingestible capsule configured to be delivered to an intestinal tract of the patient through the mouth of the patient, an ampule configured for use in an antegrade gastrointestinal (GI) delivery approach to the intestinal tract of the patient, or an ampule configured for use in a retraograde GI delivery approach to the intestinal tract of the patient.

In Example 150, the providing the kit to the clinician of any one or more of Examples 1-149 can optionally include providing a sterile kit to the clinician.

In Example 151, the providing the kit to the clinician and the providing the fecal dose to the clinician of any one or more of Examples 1-150 can optionally include using expedited shipping.

In Example 152, the expedited shipping of any one or more of Examples 1-151 can optionally include overnight shipping.

In Example 153, any one or more of Examples 1-152 can optionally include screening the patient fecal sample for at least one of a parasite, a pathogen, a disease, or an unhealthy condition of the patient.

In Example 154, any one or more of Examples 1-153 can optionally include providing a kit to the clinician, the kit enabling the clinician to store and transport a patient blood sample from the patient to the central facility, and screening the patient blood sample for at least one of a parasite, a pathogen, a disease, or an unhealthy condition of the patient.

In Example 155, the providing the kit to the clinician of any one or more of Examples 1-154 can optionally include providing a kit enabling the clinician to store and transport a wet fecal sample from the patient to the central facility.

In Example 156, the providing the kit to the clinician of any one or more of Examples 1-155 can optionally include providing a kit enabling the clinician to store, freeze, and transport the wet fecal sample from the patient to the central facility.

In Example 157, a system can include, or can optionally be combined with any portion or combination of any portions of any one or more of Examples 1-156 to include, subject matter that can include means for performing any one or more of the functions of Examples 1-156, or a machine-readable medium including instructions that, when performed by a machine, cause the machine to perform any one or more of the functions of Examples 1-156.

These non-limiting examples described above can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:
1. A bacteriotherapy bank, comprising:
a temperature specific storage device;
a plurality of human fecal samples disposed in the temperature specific storage device;
the plurality of human fecal samples including a first sample from a first donor and a second sample from a second donor different from the first donor;
wherein preparing the first sample and the second sample both include:
obtaining a donor fecal sample, and
homogenizing a donor fecal sample with the at least one cryoprotectant and then filtering the homogenized composition;
wherein the first sample includes a first dietary characteristic of the first donor;
wherein the second sample includes a second dietary characteristic of the second donor different from the first dietary characteristic of the first donor;
wherein the first dietary characteristic and the second dietary characteristic are a human donor geographic consumption region, a human donor diet, a human donor religion, or combinations thereof and are configured to be matched to a human patient based on the dietary characteristic of the human donor such that a gut microbiota of the human donor and a gut microbiota of the human patient are similar following administration of the first bacteriotherapy composition to the human patient.

2. The bacteriotherapy bank of claim 1, wherein the fecal samples are stored under temperature conditions for maintaining viability of the biota of the fecal samples.

3. The bacteriotherapy bank of claim 1, wherein the fecal samples are contained in a plurality of storage containers configured to store each of a plurality of fecal samples.

4. The bacteriotherapy bank of claim 1, wherein the first sample, the second sample, or both include a physical characteristic of the donor.

5. The bacteriotherapy bank of claim 4, wherein the physical characteristic of the donor is a donor body mass index (BMI), a donor weight, a combination of a donor height and the donor weight, or a donor body fat percentage.

6. The bacteriotherapy bank of claim 4, wherein the physical characteristic of the donor is a medical condition of the donor, or the presence or absence of a medical condition of the donor.

7. The bacteriotherapy bank of claim 1, wherein the first sample, the second sample, or both include the geographic location of the donor, the diet source of the donor, the diet type of the donor, the ethnicity of the donor, the body type of the donor, the age of the donor, the sex of the donor, the health status of the donor, the medical history of the donor, or combinations thereof.

* * * * *